United States Patent
Hauske

(10) Patent No.: US 10,485,789 B2
(45) Date of Patent: Nov. 26, 2019

(54) COMPOSITIONS AND METHODS FOR TARGETING RECEPTORS EXPRESSED IN THE GUT

(71) Applicant: Sensor Pharmaceuticals, Inc., La Jolla, CA (US)

(72) Inventor: James R. Hauske, La Jolla, CA (US)

(73) Assignee: Sensor Pharmaceuticals, Inc., La Jolla, CA (US)

( * ) Notice: Subject to any disclaimer, the term of this patent is extended or adjusted under 35 U.S.C. 154(b) by 100 days.

(21) Appl. No.: 15/328,346

(22) PCT Filed: Jul. 23, 2015

(86) PCT No.: PCT/US2015/041736
§ 371 (c)(1),
(2) Date: Jan. 23, 2017

(87) PCT Pub. No.: WO2016/014797
PCT Pub. Date: Jan. 28, 2016

(65) Prior Publication Data
US 2017/0216259 A1 Aug. 3, 2017

Related U.S. Application Data

(60) Provisional application No. 62/059,460, filed on Oct. 3, 2014, provisional application No. 62/059,357, filed on Oct. 3, 2014, provisional application No. 62/059,354, filed on Oct. 3, 2014, provisional application No. 62/028,533, filed on Jul. 24, 2014, provisional application No. 62/028,521, filed on Jul. 24, 2014, provisional application No. 62/028,538, filed on Jul. 24, 2014.

(51) Int. Cl.
| | | |
|---|---|---|
| C07D 403/14 | (2006.01) | |
| A61K 31/4192 | (2006.01) | |
| C07D 401/12 | (2006.01) | |
| C07D 405/12 | (2006.01) | |
| C07D 401/06 | (2006.01) | |
| C07D 221/18 | (2006.01) | |
| C07D 405/14 | (2006.01) | |
| C07D 211/96 | (2006.01) | |
| A61K 31/55 | (2006.01) | |
| A61K 31/404 | (2006.01) | |
| A61K 47/59 | (2017.01) | |
| A61K 31/473 | (2006.01) | |
| A61K 31/445 | (2006.01) | |
| A61K 47/60 | (2017.01) | |

(52) U.S. Cl.
CPC ........ *A61K 31/4192* (2013.01); *A61K 31/404* (2013.01); *A61K 31/445* (2013.01); *A61K 31/473* (2013.01); *A61K 31/55* (2013.01); *A61K 47/59* (2017.08); *A61K 47/60* (2017.08); *C07D 211/96* (2013.01); *C07D 221/18* (2013.01); *C07D 401/06* (2013.01); *C07D 401/12* (2013.01); *C07D 403/14* (2013.01); *C07D 405/12* (2013.01); *C07D 405/14* (2013.01)

(58) Field of Classification Search
None
See application file for complete search history.

(56) References Cited

FOREIGN PATENT DOCUMENTS

| | | | |
|---|---|---|---|
| WO | WO-99/64044 A1 | 12/1999 | |
| WO | WO-2011/123719 A2 | 10/2011 | |
| WO | WO 2015/084850 * | 6/2015 | ........... G01N 33/543 |

OTHER PUBLICATIONS

Yim et al., Bioconjugate Chem., 2009, 20, 1323-1331.*
Chatterjee et al., "Synthesis, Pharamacological Activity and Hydrolytic Behavior of Ethylenediamine and Benzathine Conjugates of Ibuprofen," Eur J Med Chem, 43: 2819-2823 (2008).
International Search Report and Written Opinion for International Application No. PCT/US2015/041736 dated Nov. 18, 2015.
Kurczab et al., "New Strategy for Receptor-based Pharmacophore Query Construction: A Case Study for 5-HT7Receptor Ligands," J Chem Inf Model, 53(12): 3233-3243 (2013).
Lees, "Dopamine Agonists in Parkinson's Disease: A Look at Apomorphine," Fundam Clin Pharmacol, 7(3-4): 121-128 (Apr. 1993).

* cited by examiner

*Primary Examiner* — Alicia L Otton
(74) *Attorney, Agent, or Firm* — Foley Hoag LLP; David P. Halstead; Laura A. Wzorek

(57) ABSTRACT

The invention relates to novel compounds and pharmaceutical preparations thereof, as well as methods of making an using these compounds. The invention further relates to methods of treating or preventing disease using the novel compounds of the invention.

9 Claims, 12 Drawing Sheets

In vivo Results

In vitro Experiments
Agonism of Gut Lumen-Expressed Molecular Targets and Whole Cell IL-1β Reduction

| Sensor Compounds | IL-1β (EC50 [uM]) | Gut Lumen-Expressed Molecular Target |
|---|---|---|
| SEN-20109 | .65 | .45 TGR-5 |
| SEN-20111 | .25 | .15 TGR-5 |
| SEN-20114 | .75 | .55 TGR-5 |
| SEN-20128 | .82 | .33 TGR-5 |

Figure 6.

In vitro Results
In vitro Experiments Measuring Reduction of Pro-Inflammatory Cytokines
Phenotypic Screen: Whole Cell Reduction of IL-6 and TNFα

| Sensor Compounds | IL-6 (EC50 [uM]) | TNFα |
|---|---|---|
| SEN-82343 | .35 | .65 SHP7 |
| SEN-25042 | .15 | .45 TLR-4 |
| SEN-20130 | .25 | .75 TGR-5 |
| SEN-20128 | .12 | .43 TGR-5 |

COMPOSITIONS AND METHODS FOR TARGETING RECEPTORS EXPRESSED IN THE GUT

RELATED APPLICATIONS

This application is the United States National Stage application of PCT/US2015/041736, filed Jul. 23, 2015, which claims the benefit of priority to U.S. Patent Application Ser. Nos. 62/028,533, filed Jul. 24, 2014; 62/028,521, filed Jul. 24, 2014; 62/028,538, filed Jul. 24, 2014; 62/059,354, filed Oct. 3, 2014; 62/059,357, filed Oct. 3, 2014; and 62/059,460, filed Oct. 3, 2014, the contents of which are hereby incorporated by reference.

BACKGROUND

Gut mucosal surfaces bear many receptors, sensitive to nutrients and other signaling molecules that reflect changing conditions in the environment of the gut. Modulation of these receptors can have effects ranging from local (modulating intestinal inflammation) or intuitive (modulating hunger and satiety) to systemic (diabetes) or neurological (depression). However, many compounds that effectively modulate these receptors to beneficial effect in the gut cause adverse effects when these compounds are absorbed and affect receptors elsewhere in the body. Improved methods for selectively targeting gut receptors are needed.

SUMMARY OF INVENTION

The present invention provides compounds and methods for selectively modulating a gut-expressed biological target, such as a receptor, by displaying receptor modulators on scaffolds that are not absorbed into the bloodstream.

In certain embodiments, the invention provides compounds comprising:
a scaffold having a plurality of branches, wherein each of a plurality of branches terminates in a pharmacophore having an affinity for a receptor expressed in a gastrointestinal tract; or a pharmaceutically acceptable salt thereof;
wherein bonds linking the pharmacophores to the scaffold are not hydrolyzed under physiologic conditions; and
wherein the compound weighs less than about 10,000 Daltons.

The invention also provides pharmaceutical compositions of the compounds of the invention.

In certain embodiments, the invention provides methods for treating metabolic syndrome or a disorder associated with metabolic syndrome in a subject in need thereof, comprising administering to the subject a compound of the invention. The invention also provides methods of administering the compound to a subject suffering from metabolic syndrome or a disorder associated with metabolic syndrome.

In certain embodiments, the invention also provides methods of making a compound of the invention, comprising contacting a scaffold having a plurality of branches, wherein each of a plurality of branches terminates in a first reactive moiety, with a plurality of linking molecules, each linking molecule comprising a pharmacophore linked to a second reactive moiety, under conditions sufficient to induce a coupling reaction, such as a cycloaddition, between the first reactive moiety and the second reactive moiety.

FIGS. 1-3 describe various embodiments of the invention and methods of preparing compounds of the invention, but are intended to be exemplary and not limiting in any way.

BRIEF DESCRIPTION OF THE DRAWINGS

Figures 4, 5:
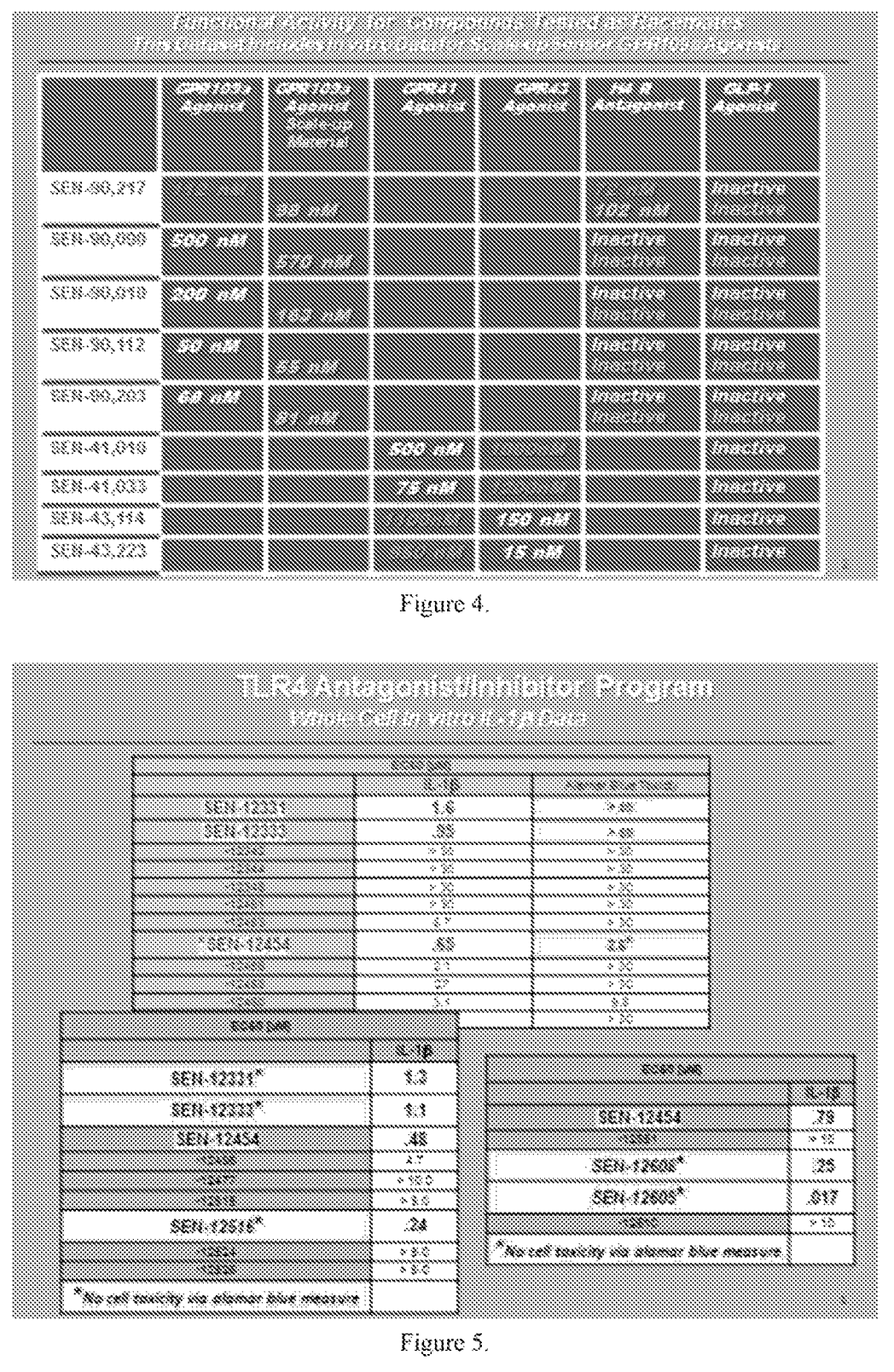

FIG. 4 is a table containing in vitro data for exemplary gut-restricted compounds of the invention.

FIG. 5 contains tables of whole cell in vitro data for reduction of cytokine IL-1$\beta$ using exemplary gut-restricted TLR4 antagonists.

FIG. 6 is a table showing in vitro data for reduction of cytokine IL-1$\beta$ using exemplary gut-restricted compounds of the invention.

FIG. 7 is a table showing in vitro data for reduction of cytokines IL-6 and TNF-$\alpha$ using exemplary gut-restricted compounds of the invention.

DETAILED DESCRIPTION OF THE INVENTION

Figure 1:
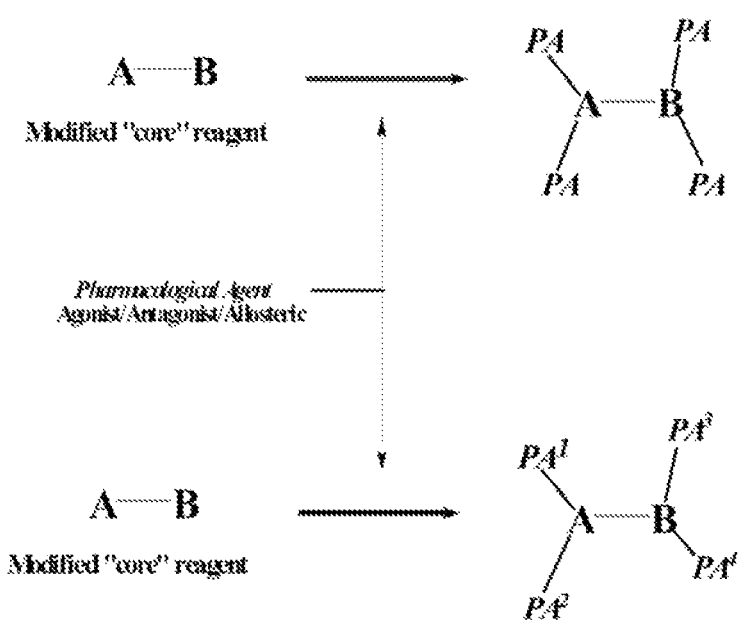
FIG. 1 depicts a general structure of a pharmacophore-appended scaffold of the invention.

In one aspect, the invention provides a compound weighing less than about 10,000 Daltons (preferably less than about 7500 Da, less than about 5000 Da, less than about 3000 Da, or even less than about 2000 Da), comprising a scaffold having a plurality of branches (preferably at least 3, or 4, 5, or more branches), wherein some or all of the branches (preferably at least 3, or 4, 5, or more branches) terminate in a pharmacophore having an affinity for a biological target expressed in a gastrointestinal tract, or a pharmaceutically acceptable salt thereof. In certain embodiments, the compound is dendrimer, e.g., where the branches are identical or similar (e.g., differing primarily in the terminal pharmacophore).

The scaffold is a molecular framework for joining the various branches and pharmacophores, and may be oligomeric, dendritic, cyclic, acyclic, branched, linear, or any other suitable form for covalently linking the various elements of the compound together. Similarly, the branches may be long or short, cyclic or acyclic, or any other suitable configuration for covalently linking the pharmacophores to the scaffold. The primary function of the scaffold and branches is to present the pharmacophores in an environment that is sterically unhindered enough for the pharmacophore to interact with its target receptor. Thus, a compact scaffold (e.g., a glucose ring, where branches can be coupled to neighboring hydroxyl groups) may be paired with longer branches to avoid steric crowding of the pharmacophores, while a scaffold with greater spacing between branching points (e.g., an oligomeric chain formed by reacting epichlorohydrin and ethylene glycol) may be able to utilize shorter branches without compromising interaction of the pharmacophores with their target receptors. In certain embodiments, each branch terminates in a pharmacophore. In certain embodiments, at least one branch does not terminate in a pharmacophore.

The pharmacophores are chemical moieties capable of interacting with (e.g., activating or inactivating, agonizing or antagonizing) a biological receptor, preferably on a selective basis. In some embodiments, a pharmacophore is essentially a drug molecule that is covalently attached to the rest of the compound; that is, a pharmacophore, severed from its branch and scaffold, retains its ability to interact with the receptor that it targets as part of the compound and has biological activity of its own.

For any given molecule of the compound, the pharmacophores can be identical for all branches that terminate in a pharmacophore, or some branches may terminate in one pharmacophore while other branches terminate in a different pharmacophore. In some embodiments, each branch terminates in a different pharmacophore. Different pharmacophores of a molecule may target the same receptor or different receptors expressed in the gut. In certain embodiments, pharmacophores are displayed on the scaffold in an arrangement that permits two or more pharmacophores of a compound to simultaneously interact with two or more target receptors on the surface of a single cell. When a compound comprises at least two different pharmacophores, administering the compound may provide an additive therapeutic effect (or even a synergistic therapeutic effect) relative to the therapeutic effect of administering a mixture of analogous compounds where each pharmacophore of a compound is the same, but the mixture provides pharmacophores in the same ratio present in the multi-pharmacophore compound (in other words, as though the pharmacophores of the multi-pharmacophore compound were redistributed among scaffolds such that the pharmacophores of a single scaffold were all identical, but the mixture of scaffolds comprises the same pharmacophores in corresponding proportions and amounts as in the multi-pharmacophore compound).

In certain embodiments, one or more pharmacophores affect the expression level of one or more inflammatory cytokines in gut mucosal cells. Inflammatory cytokines include, but are not limited to IL-1beta, IL-6, TNF-alpha, or IL-1β. In certain embodiments, the precise nature of the specific gut-lumen expressed molecular target is not defined. In certain embodiments, one or more pharmacophores decrease the expression of one or more inflammatory cytokines such as IL-1beta, IL-6, or TNF-alpha.

In certain embodiments, one or more pharmacophores have an affinity for a biological target. Such biological targets include, but are not limited to receptors, ion channels, and transporters. In certain embodiments, the receptor is a PRR-type receptor (Pattern Recognition Receptor), such as a TLR-type receptor. In certain embodiments, one or more pharmacophores have an affinity for a bile acid receptor, taste receptor, olfactory receptor, TGR-type, or GPR-type receptor.

In certain embodiments, one or more pharmacophores have an affinity for receptor such as Bradykinin $B_2$, GPR40, GPR43, GPR109A, GPR120, a taste receptor such as T1R1, T1R2, T1R3, T2R13, an olfactory receptor such as OR2A4, α-Gustducin, GPCRC6A, GPR55, and GPR92.

In certain embodiments, one or more pharmacophores have an affinity for receptor such as TLR-4, Bradykinin $B_2$, GPR40, GPR43, GPR109A, GPR120, a taste receptor such as T1R1, T1R2, T1R3, T2R13, an olfactory receptor such as OR2A4. α-Gustducin, GPCRC6A, GPR55, and GPR92.

In certain embodiments, one or more pharmacophores have an affinity for receptor such as Bradykinin $B_2$, $5HT_7$, GPR40, GPR43, GPR109A, GPR120, a taste receptor such as T1R1, T1R2, T1R3, T2R13, an olfactory receptor such as OR2A4, α-Gustducin, GPCRC6A, GPR55, and GPR92.

In certain embodiments, one or more pharmacophores have an affinity for receptor such as Bradykinin $B_2$, GPR40, GPR43, GPR109A, GPR120, Histamine $H_4$, a taste receptor such as T1R1, T1R2, T1R3, T2R13, an olfactory receptor such as OR2A4, α-Gustducin, GPCRC6A, GPR55, and GPR92.

In certain embodiments, one or more pharmacophores have an affinity for receptor such as TLR-4, Bradykinin $B_2$, $5HT_7$, GPR40, GPR43, GPR109A, GPR120, Histamine $H_4$, a taste receptor such as T1R1, T1R2, T1R3, T2R13, an olfactory receptor such as OR2A4, α-Gustducin, GPCRC6A, GPR55, and GPR92.

In certain embodiments, one or more pharmacophores have an affinity for surface-attached enzymes such as α-glucosidase and Ghrelin O-acyl Transferase, ion channels such as TRPV4, or transporters such as SGLT-3 and GLUT-2.

In certain embodiments, one or more pharmacophores have an affinity for a TLR-4 receptor.

In certain embodiments, one or more pharmacophores have an affinity for a $5HT_7$ receptor.

In certain embodiments, one or more pharmacophores have an affinity for a Histamine $H_4$ receptor.

Figure 2:
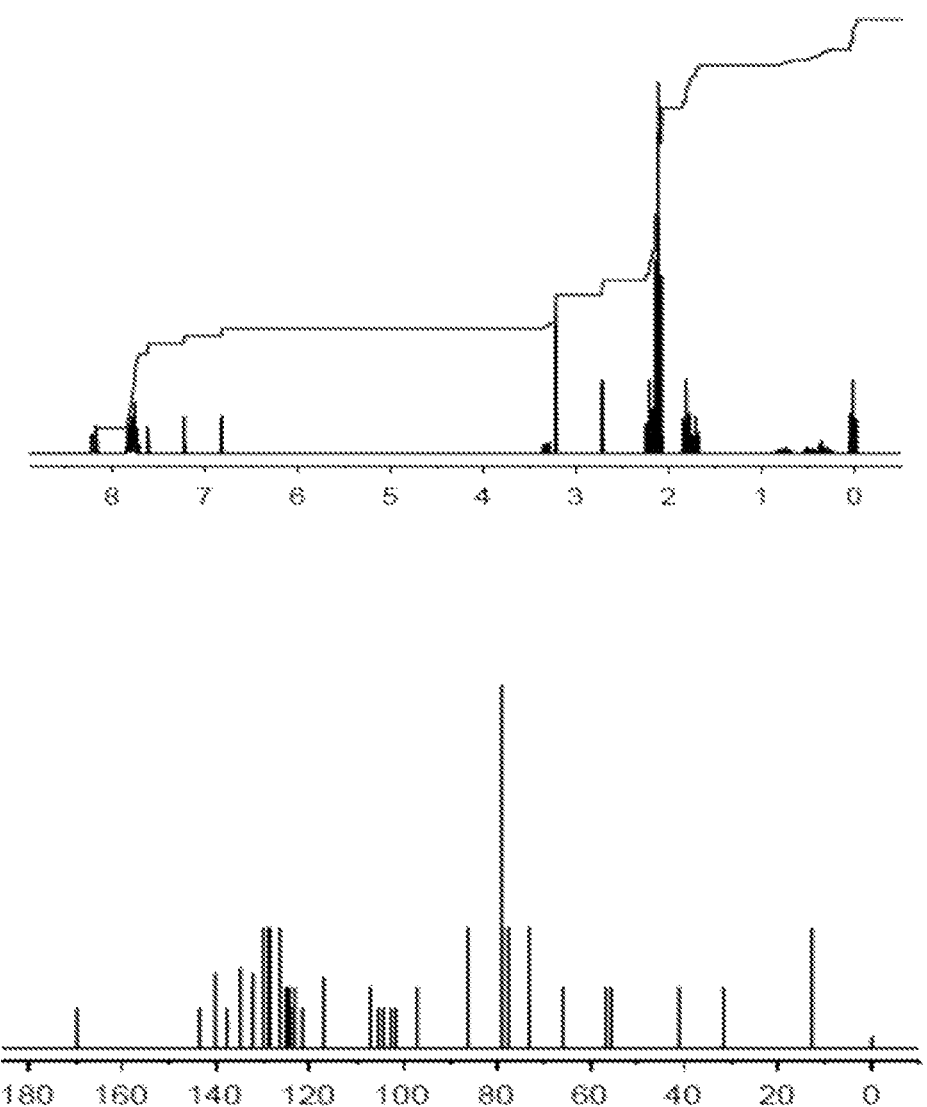
FIG. 2 depicts characterization data for a compound of the invention.
Figure 3:
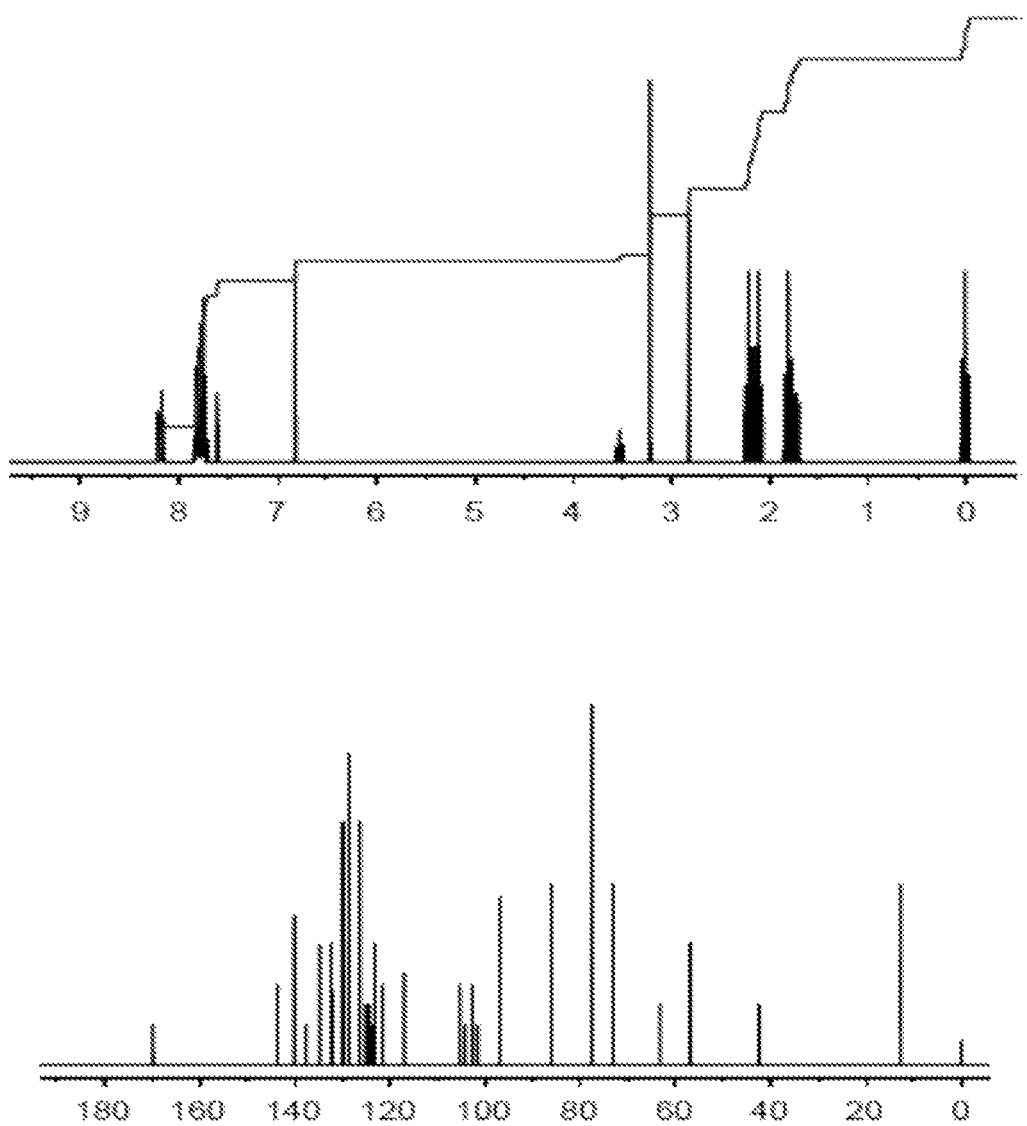
FIG. 3 depicts characterization data for a compound of the invention.
Figure 8:
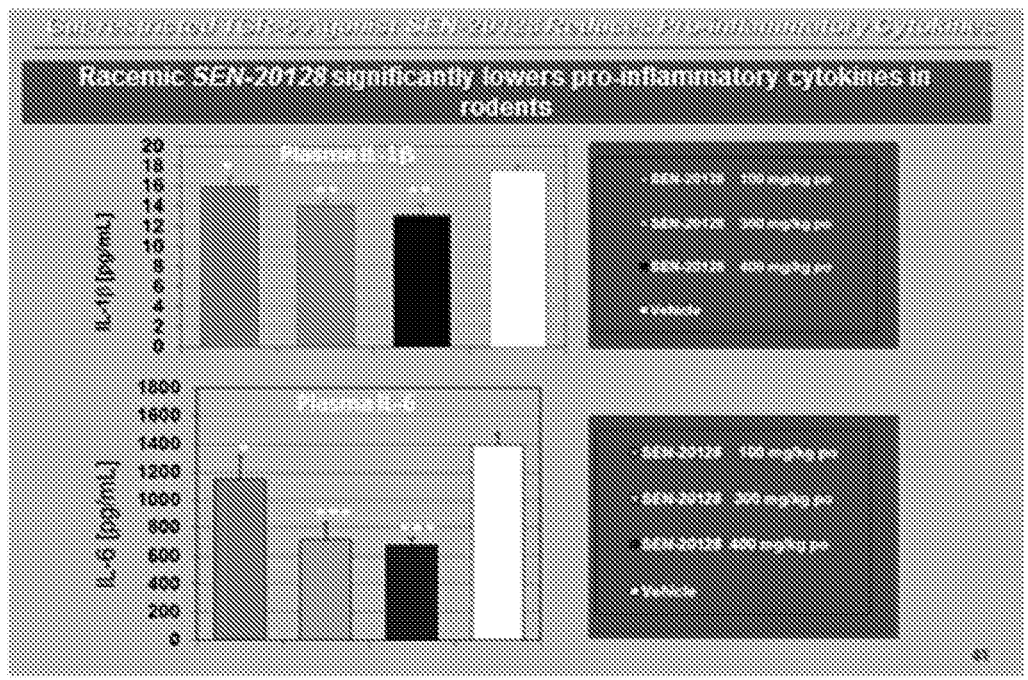
FIG. 8 contains a series of bar graphs that show reduction of pro-inflammatory cytokines IL-1$\beta$ and IL-6 using a gut-restricted TGR-5 agonist compound of the invention.
Figure 9:
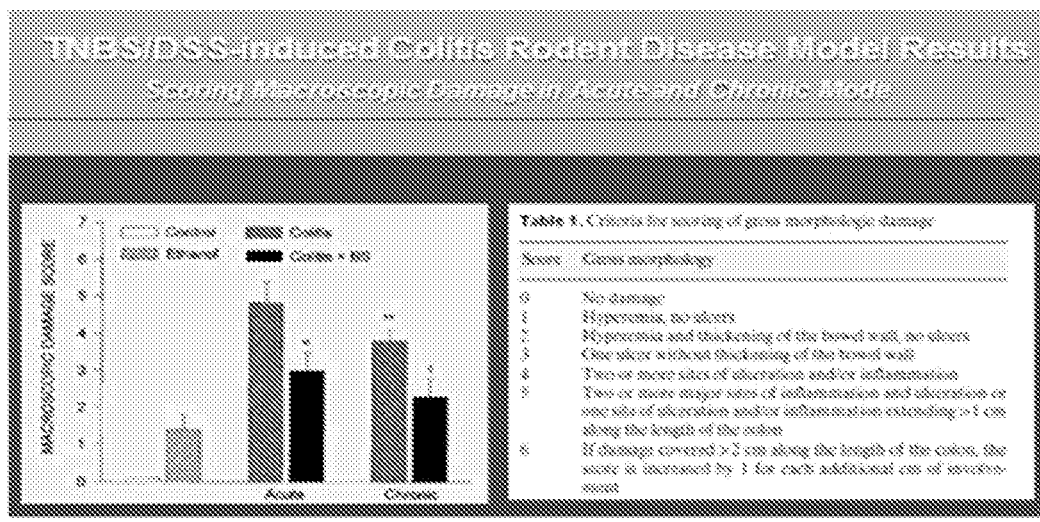
FIG. 9 is a bar graph demonstrating damage scores in a TNBS/DSS-induced colitis model.
Figure 10:
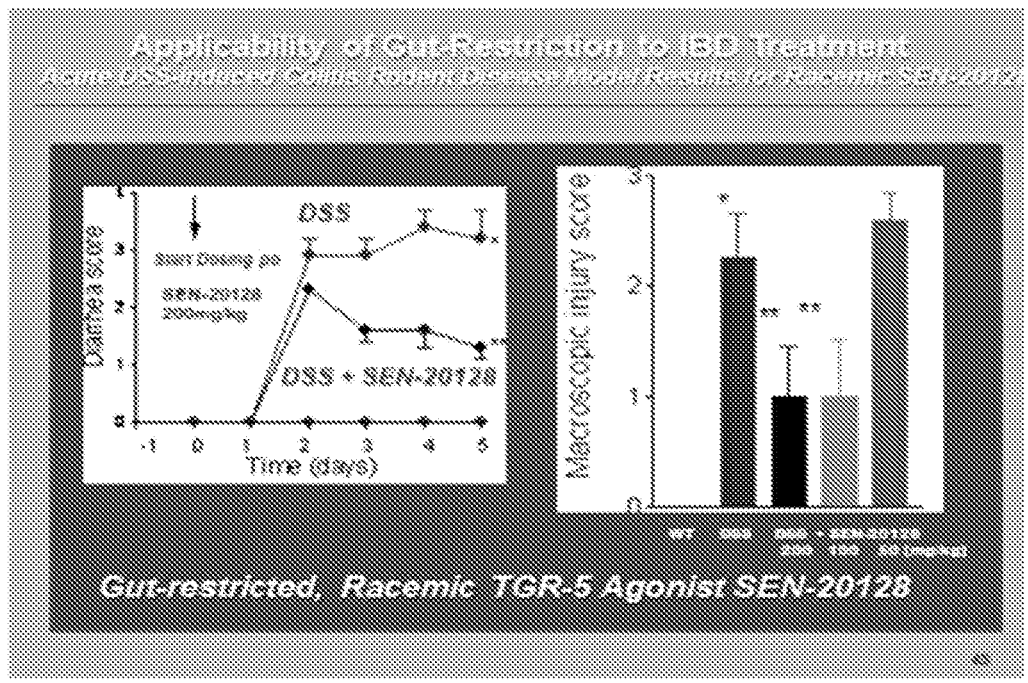
FIG. 10 contains charts that show in vitro results of administration of a gut-restricted compound of the invention in a DSS-induced colitis model.
Figure 11:
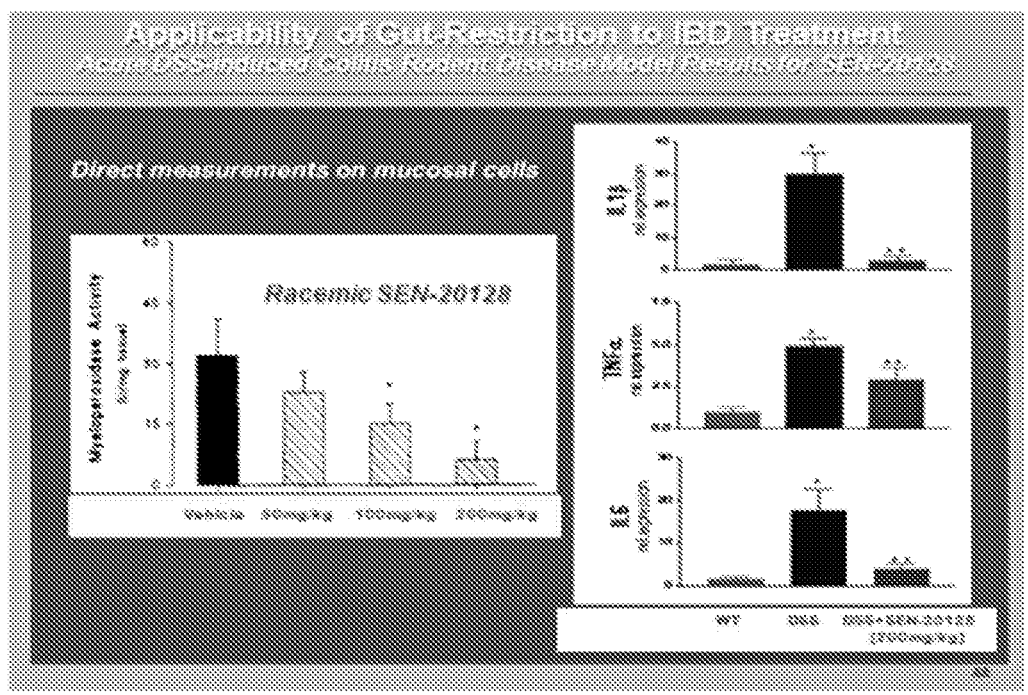
FIG. 11 contains bar graph that show in vitro results of administration of a gut-restricted compound of the invention in a DSS-induced colitis model.
Figure 12:
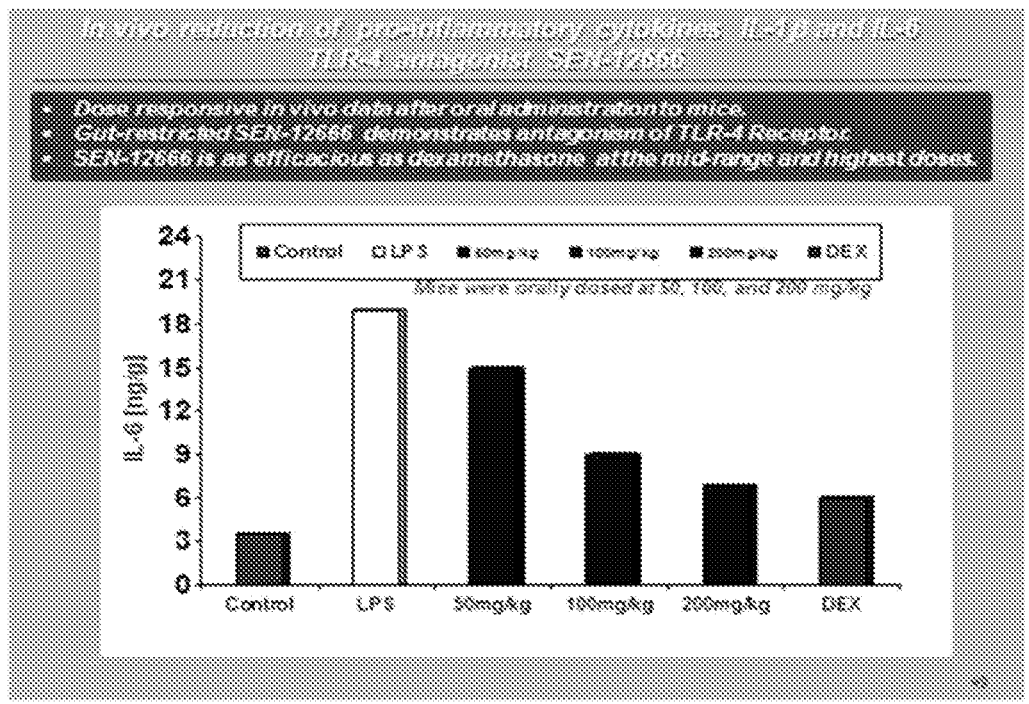
FIG. 12 contains a bar graph that demonstrates the in vivo reduction of pro-inflammatory cytokines IL-6 using a gut-restricted TLR-4 antagonist compound of the invention.
Figure 13:
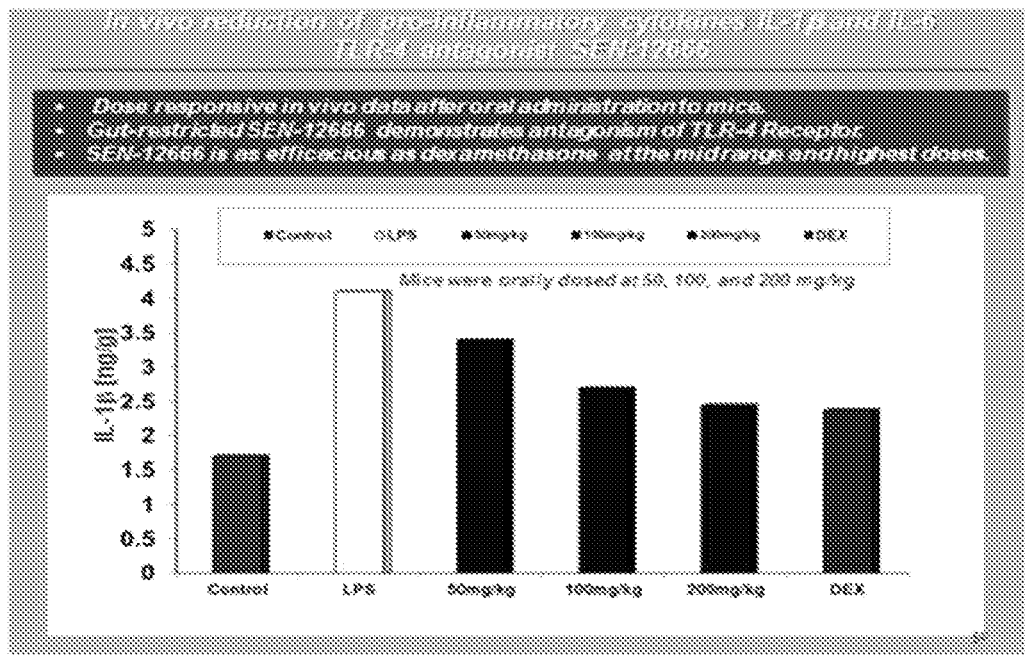
FIG. 13 contains a bar graph that demonstrates the in vivo reduction of pro-inflammatory cytokines IL-1$\beta$ using a gut-restricted TLR-4 antagonist compound of the invention.
Figure 14:
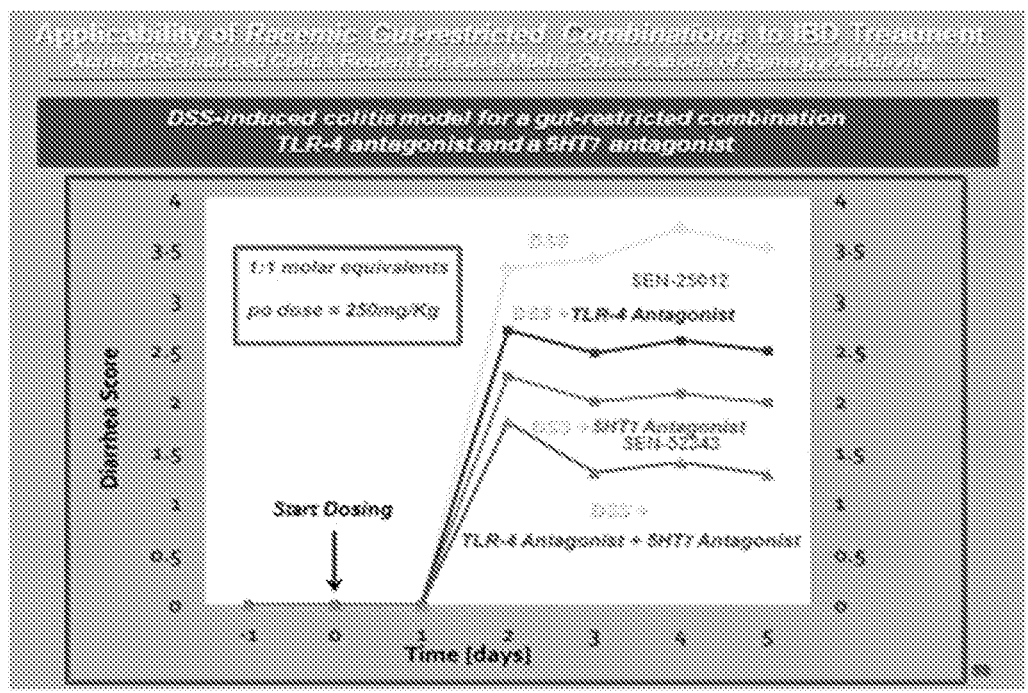
FIG. 14 is a chart that shows in vim efficacy of a colitis treatment regimen using a gut-restricted TLR-4 antagonist and a 5HT$_7$ antagonist compound of the invention.
Figure 15:
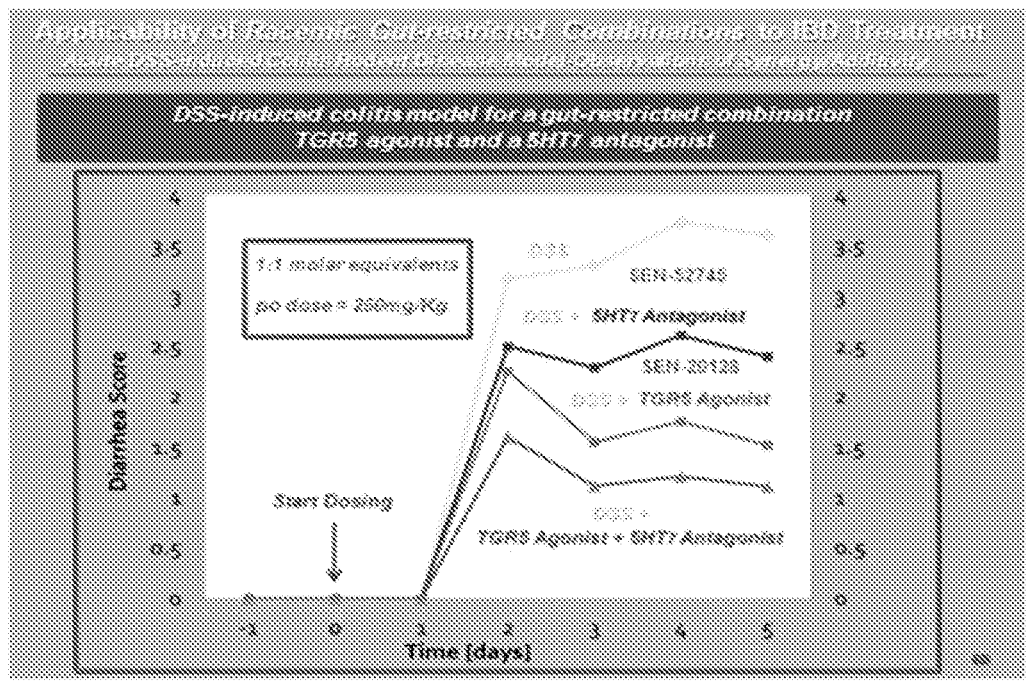
FIG. 15 is a chart that shows in vivo efficacy of a colitis treatment regimen using a gut-restricted TGR5 agonist and a 5HT$_7$ antagonist compound of the invention.
Figure 16:
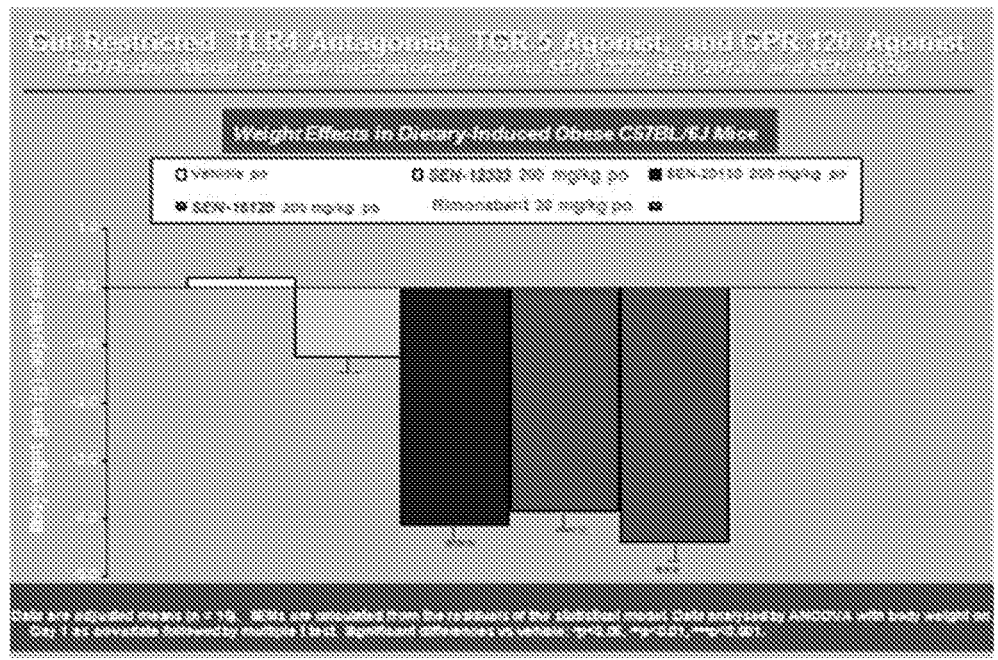
FIG. 16 is a bar graph that provides the weight effects of administration of a TLR4 antagonist, a TGR-5 agonist and a GPR-120 agonist.
Figure 17:
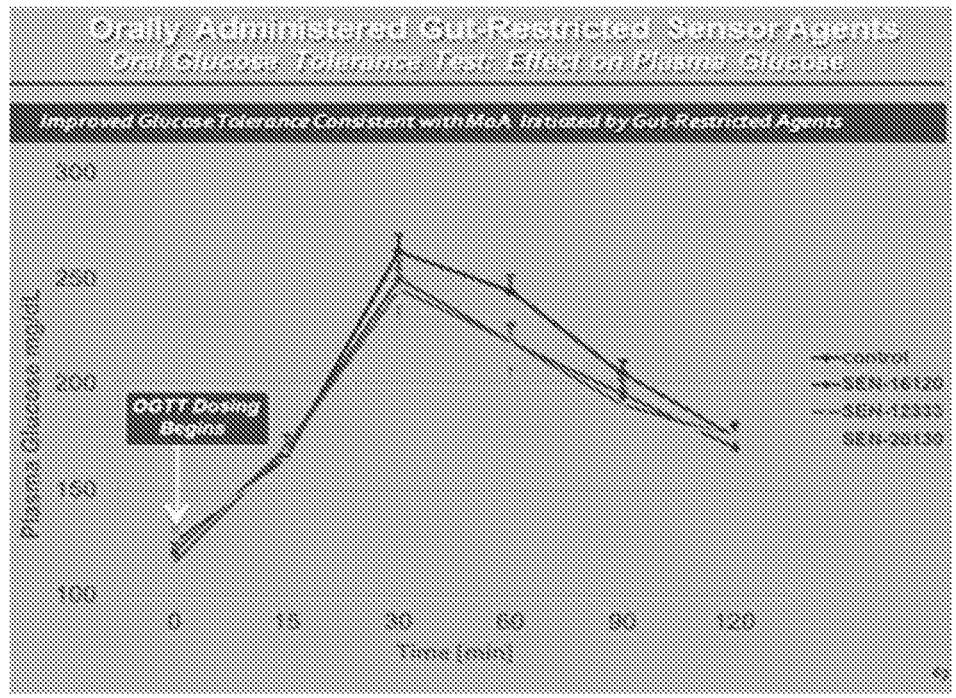
FIG. 17 is a chart that shows the effects of oral-administration of a gut-restricted compound of the invention on plasma glucose levels.
Figure 18:
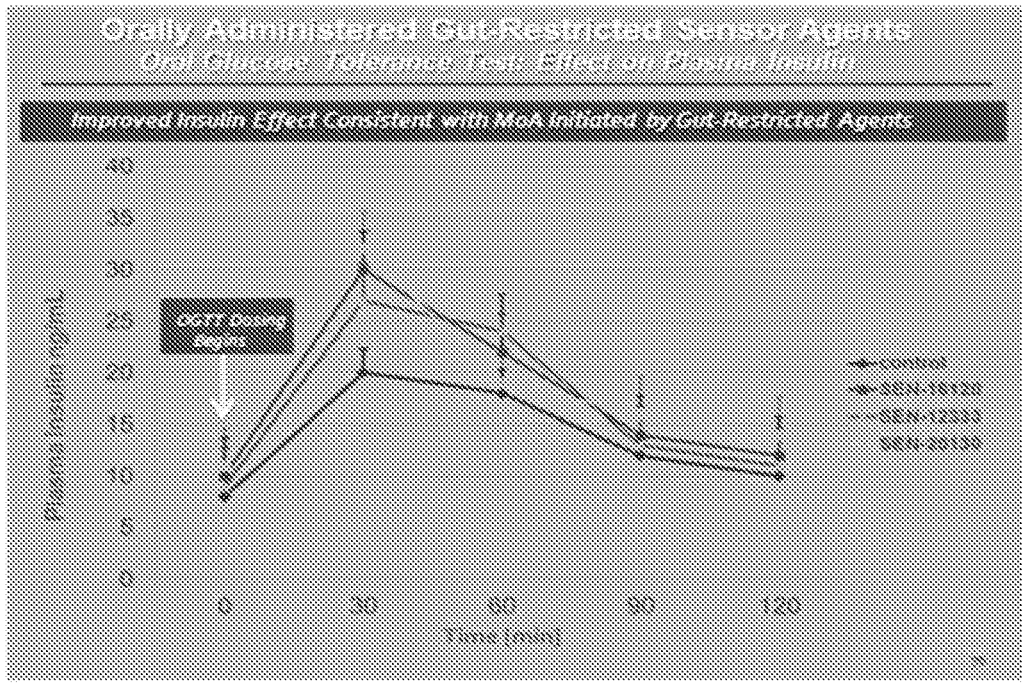
FIG. 18 is a chart that shows the effects of oral-administration of a gut-restricted compound of the invention on plasma insulin levels.
Figure 19:
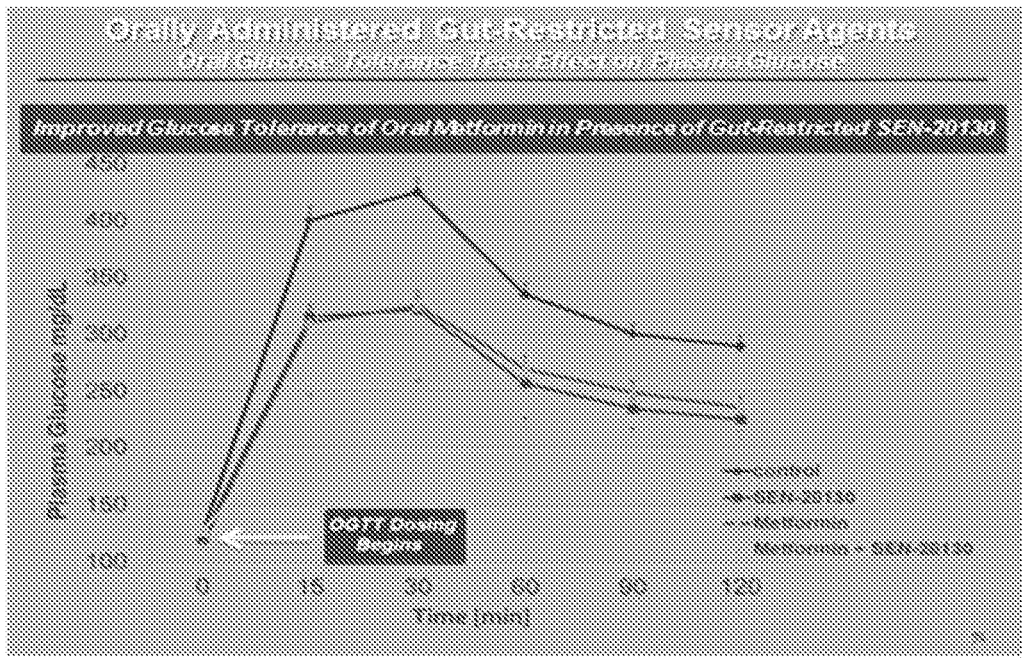
FIG. 19 is a chart that shows the effects of oral-administration of a gut-restricted compound of the invention on plasma glucose levels.
Figure 20:
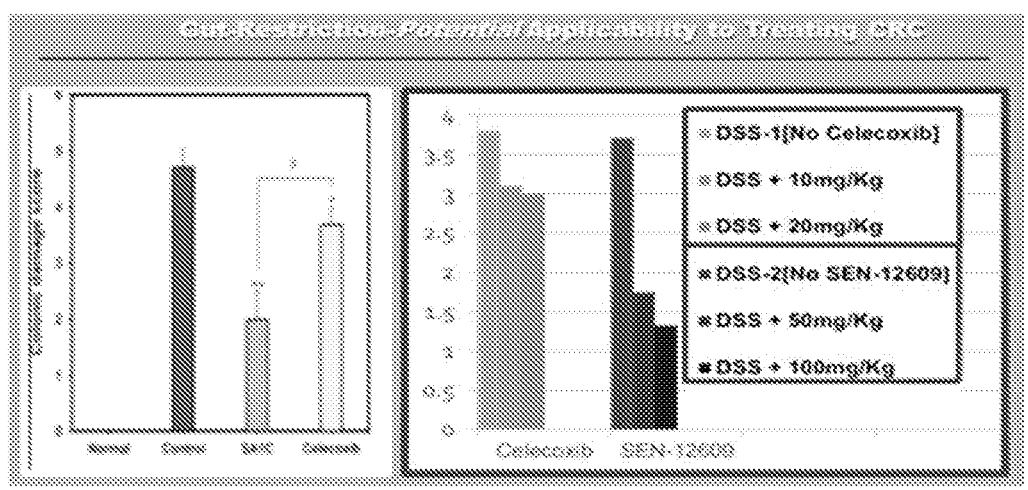
FIG. 20 contains bar graphs that demonstrate the potential for the gut-restricted compounds of the invention to be applied to treating colorectal cancer.

Particular embodiments of the compounds of the invention are described herein and in FIGS. 1-3. In certain embodiments, the pharmacophores that are incorporated into the compounds of the invention are derived from bioactive drug compounds. In certain embodiments, the pharmacophore moieties are related to the parent structure of the bioactive drug compounds by chemical modification (e.g., substitution) of the parent structure. In example embodiments, a parent structure is be modified by a linking moiety that effectively attaches the pharmacophore to a scaffold, as described herein.

Modifications of bioactive drug compound include substitution, truncation, stereocenter inversion, isomerization, or hybridization change. In certain embodiments, a bioactive drug compound is substituted at any substitutable position, including a heteroatom (e.g., O, N, S, Sc, P), a hydrogen-bearing $sp^2$-hybridized carbon, or a hydrogen-bearing $sp^3$-hybridized CH.

A person of ordinary skill in the art would appreciate that a bioactive drug compound can be incorporated as a pharmacophore into the compounds of the invention in any one of a variety of spatial orientations, and at any one of a variety of substitutable positions, as described herein. A person of ordinary skill in the art can readily synthesize a number of such compounds in order to determine which orientations and connectivities exhibit acceptable biological activity for a given application. In example embodiments, a compound with a pharmacophore having appropriate orientation and connectivity retains the type of biological activity of the parent bioactive drug compound, though the activity of the compound bearing the pharmacophore may be stronger or weaker than that of the parent bioactive drug compound. In certain embodiments, a suitable orientation and connectivity is determined when the pharmacophore exhibits at least 99%, 98%, 95%, 90%, 85%, 80%, 75% 70%, 65%, 60%, 55%, or 50% of the biological activity of parent compound.

In example embodiments, the pharmacophore moiety is derived from olopatadine or aminptine. Schemes 1A and 1B, below, show synthetic routes for exemplary compounds of the present invention. These compounds illustrate the conceptual approach for utilizing drug molecules as pharmacophores in the compounds and methods described herein.

Scheme 1A:

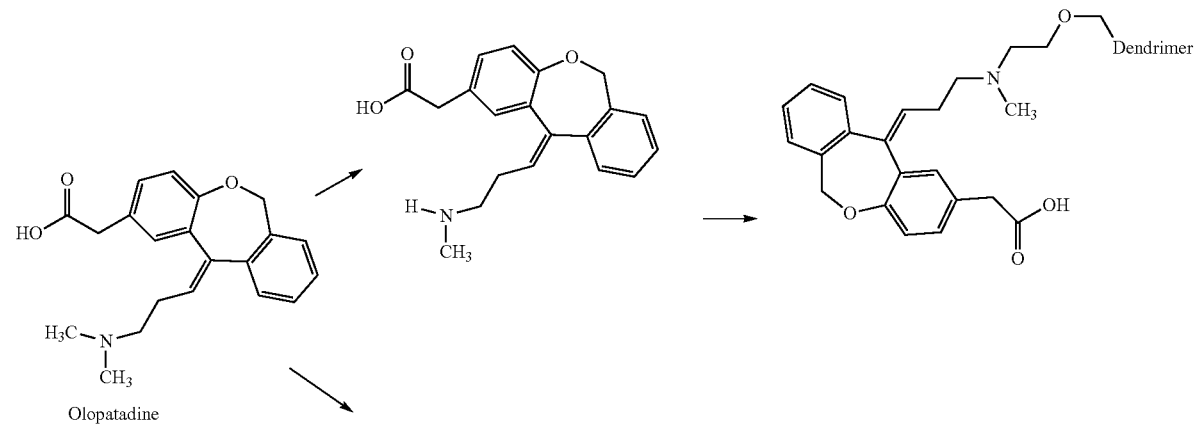

Olopatadine

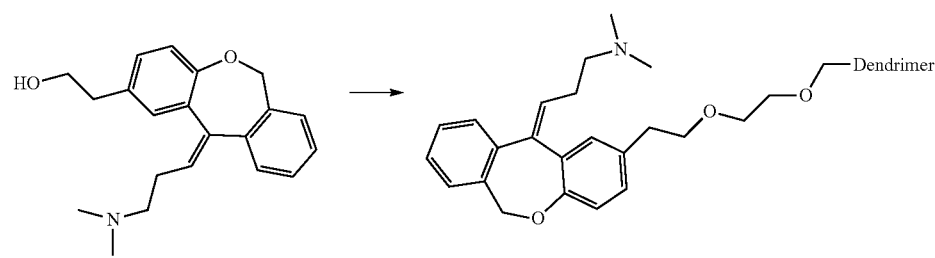

Scheme 1B:
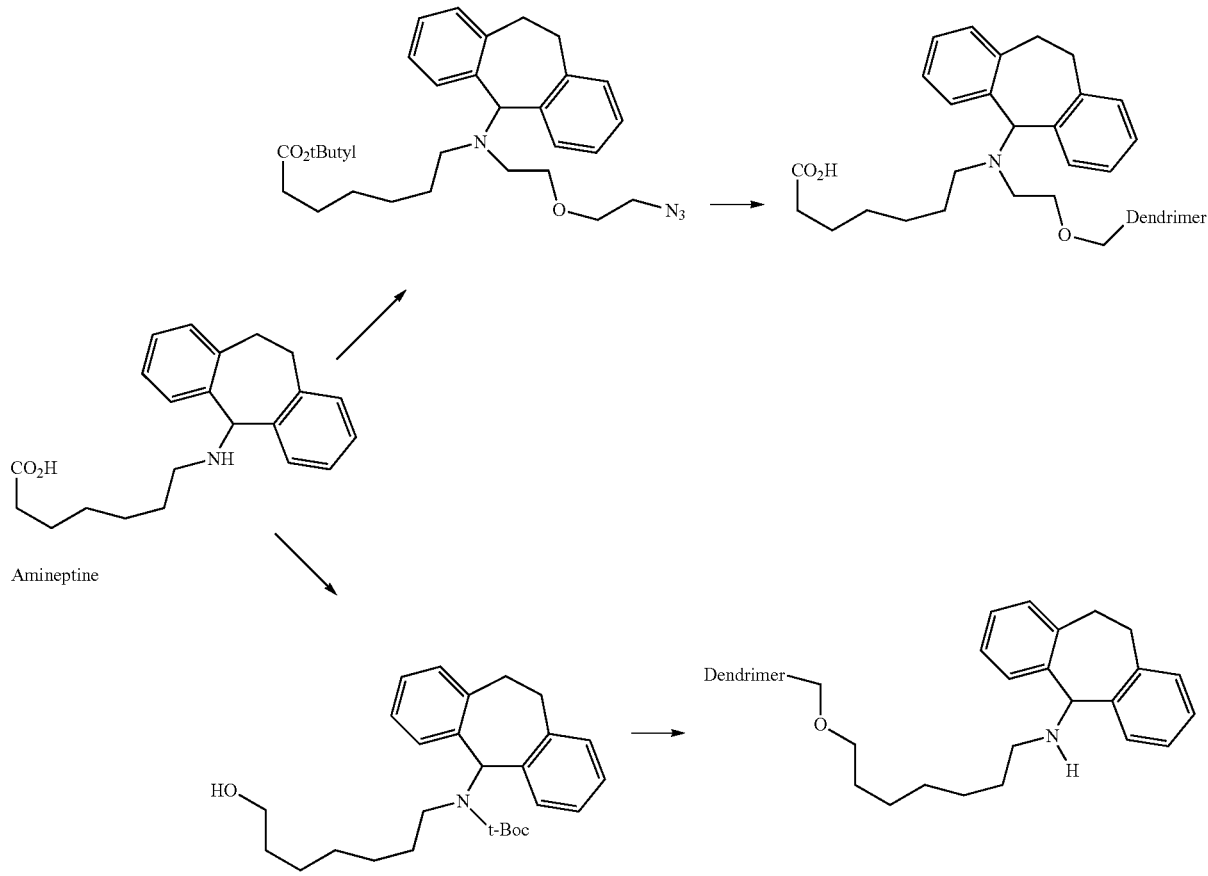
Scheme 1C provides further exemplary compounds of the invention.
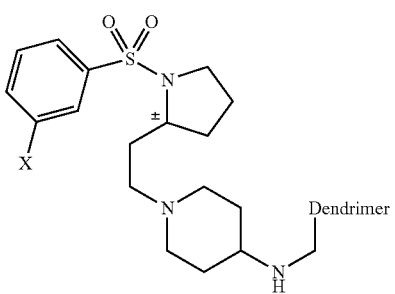
X = F, SEN-52282; antagonist EC$_{50}$ = 175 nM
X = OH, SEN-52745; antagonist EC$_{50}$ = 400 nM
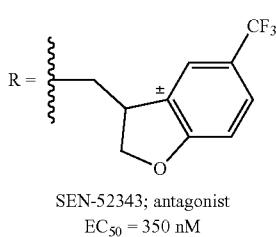
SEN-52343; antagonist
EC$_{50}$ = 350 nM
-continued
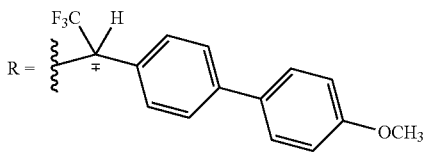
SEN-52444; antagonist
EC$_{50}$ = 875 nM
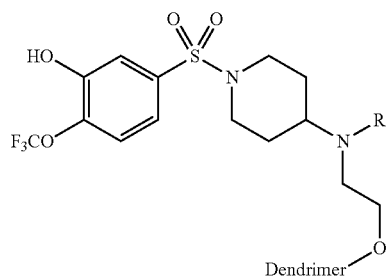

In example embodiments of the compounds of the invention, at least one pharmacophore is
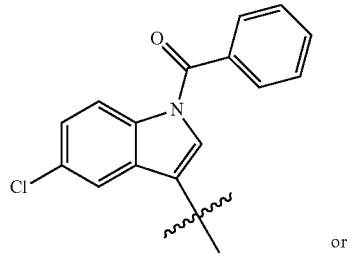
or
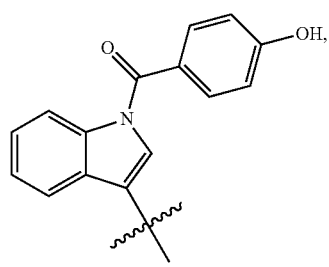
wherein
indicates a point of attachment to a branch.
In example embodiments of the compounds of the present invention, at least one pharmacophore has a structure selected from
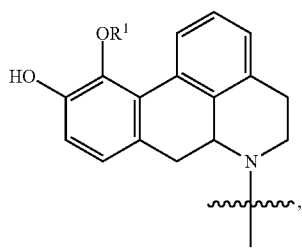
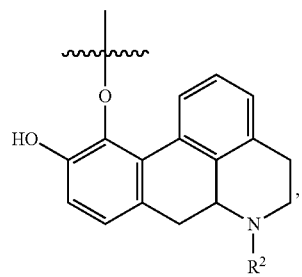
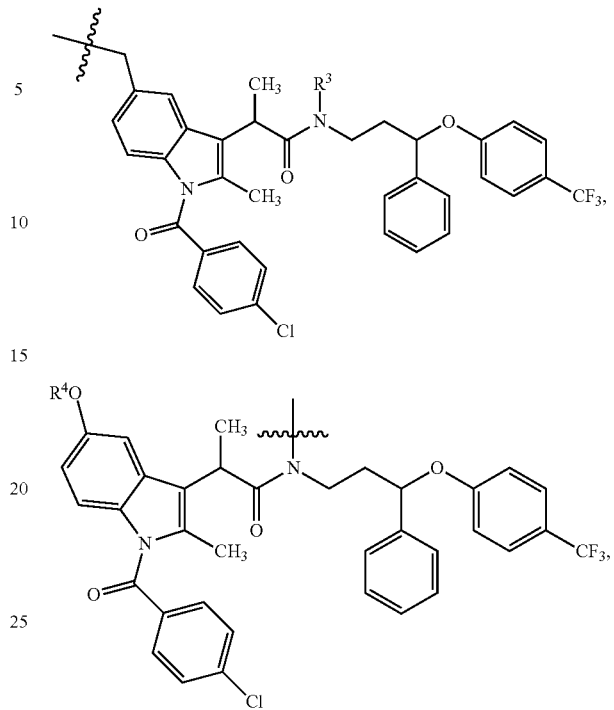
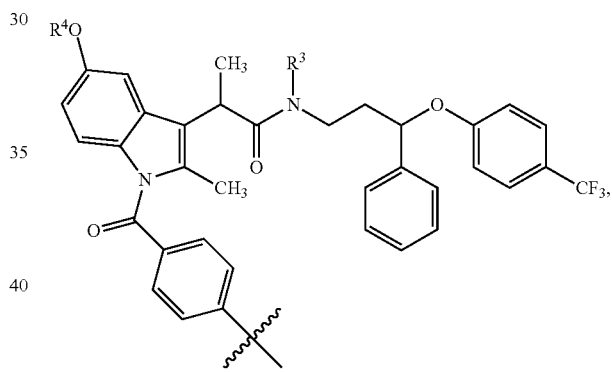
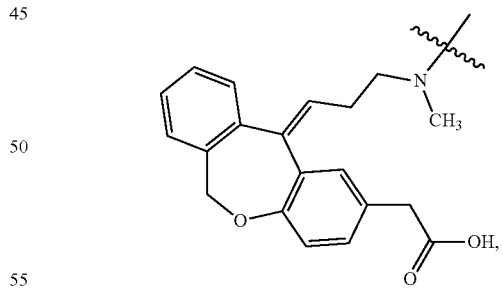
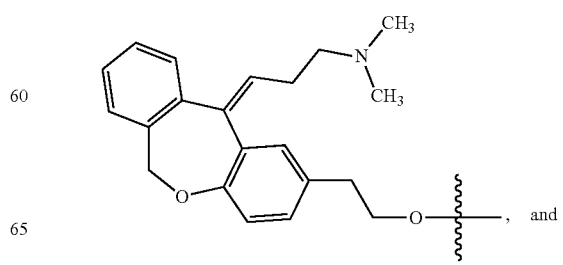
, and -continued

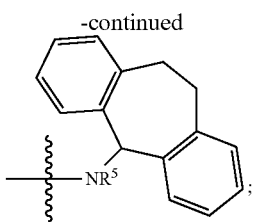

wherein

indicates a point of attachment to a branch;

$R^1$, $R^2$, $R^3$, and $R^4$ are selected from H, $(C_{1-6})$alkyl, and $(C_{6-10})$aryl; and $R^5$ is H or $(C_{1-10})$alkyl, optionally substituted with hydroxyl, carboxyl, amide, or amido.

In example embodiments, the compounds of the invention are TLR-4 antagonists.

In further example embodiments of the compounds of the invention, at least one pharmacophore has a structure selected from

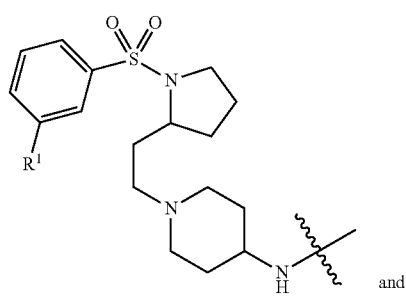

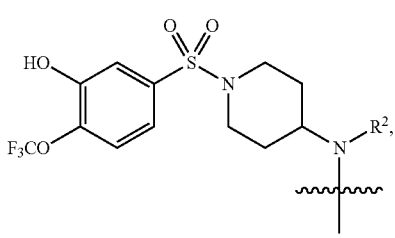

wherein

indicates a point of attachment to a branch;
$R^1$ is halogen or hydroxyl; and
and $R^2$ is

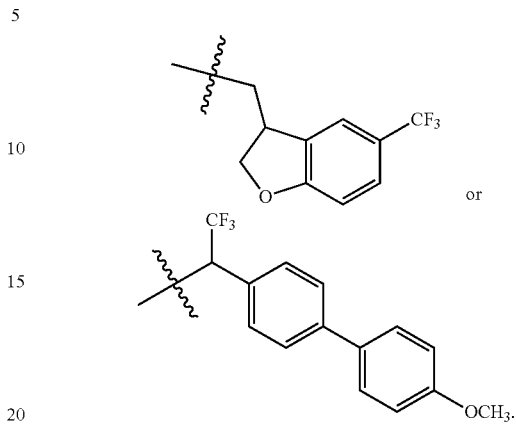

In example embodiments, the compounds of the present invention are $5HT_7$ antagonists.

Typically, the compound is configured to be substantially stable to the conditions of the gastrointestinal tract (including pH and digestive enzymes), e.g., such that the pharmacophores are not released from the scaffold during passage through the gastrointestinal tract. For example, bonds that link the pharmacophores to the scaffold are preferably not hydrolyzed under physiologic conditions (e.g., lack ester, thioester, acetal, ketal, or other acid- or base-labile bonds).

In some embodiments, it is advantageous to selectively target receptors in one portion of the gut and not in other portions of the gut, e.g., to target receptors in the intestines but not the stomach. While this can be accomplished by formulating the compound in an enteric coating that is resistant to stomach acid but dissolved in the basic environment of the intestine, it can also be accomplished by covalently modifying the pharmacophores with a masking moiety that a) blocks interaction of the pharmacophore with its target receptor and b) is resistant to the acid environment of the stomach but readily cleaved in the basic conditions of the intestine. Modification of the pharmacophore renders the compound a prodrug. For example, a hydroxyl group of a pharmacophore could be esterified with 4-amino-butanoic acid. In the acidic environment of the stomach, the amino group would be protonated, masking its nucleophilicity; in the basic environment of the intestine, the amino group would be deprotonated, leading to intramolecular cyclization, generating a lactam and revealing the pharmacophore hydroxyl. Compounds that undergo reactions of this sort, without cleaving the pharmacophore from the scaffold, are still considered to be substantially stable in the gastrointestinal tract.

While molecular size is one factor that can contribute to a molecule's resistance to absorption into the bloodstream from the gastrointestinal tract, charge and polarity can play an important role as well. A hydrophobic surface of the compound helps inhibit uptake of the compounds into the bloodstream, and so preferably the pharmacophores are selected to be relatively non-polar or hydrophobic, i.e., lacking ionizable moieties (such as carboxylic acid or amino groups). However, to assist in solubilizing the compound in the digestive tract, the scaffold and/or branches may be hydrophilic or even ionizable, and preferably include one or more amino, guanidino, or other moieties (e.g., nitrogen-containing heterocyclic or heteroaryl rings (such as morpholino, piperidino, piperazino, pyridyl, pyrimidyl, imidazolyl, pyrrolyl, pyrazinyl, oxazolyl, thiazolyl, isoxazolyl, triazolyl, etc.) that are protonated at least under the acidic conditions of the stomach and at neutral pH, if not also in the comparatively basic environment of the intestine. Thus, in certain embodiments, each branch comprises an optionally substituted heterocycle, such as a nitrogen-containing heterocycle. In certain such embodiments, each branch independently comprises —Y($C_{1-20}$)alkyl- or —Y—($CH_2CH_2X)_n$—, wherein:

X, independently for each occurrence, represents O, S, SO, $SO_2$, NH, N($C_{6-14}$ aryl), N($C_{1-20}$)alkyl), or N(($C_{1-20}$)alkyl ($C_{6-14}$ aryl));

Y is, independently for each occurrence, an optionally substituted heterocycle, such as a nitrogen-containing heterocycle, and n is an integer from 1 to 20.

Suitable heterocycles include optionally substituted isoxazoline, isoxazolidine, pyrazoline, imidazoline, or triazole.

In certain particular embodiments, the compound has a structure of the formula:

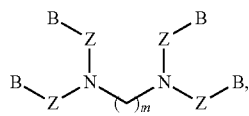

wherein:

Z represents, independently for each occurrence, a bond, ($C_{1-10}$)alkyl, ($C_{6-14}$)aryl, ($C_{6-14}$)aryl($C_{1-10}$)alkyl, ($C_{2-10}$) alkenyl, or ($C_{2-10}$)alkynyl;

B represents a branch, optionally terminating in a pharmacophore; and m is an integer from 0 to 10.

In another aspect, the invention provides pharmaceutical compositions of the compounds described herein, optionally in admixture with one or more pharmaceutically acceptable excipients. Preferably, the compositions are suitable for oral administration, whether solids (tablets, capsules, caplets, etc.), liquids (suspensions, solutions, etc.), or other orally administered formulations (dissolving films, lozenges, chewing gum, etc.).

In yet another aspect, the invention provides methods for administering the compounds and compositions described herein, e.g., for the treatment of metabolic syndrome or a disorder associated with metabolic syndrome in a subject in need thereof.

In yet another aspect, the invention provides methods for making the compounds and compositions disclosed herein, e.g., by:

contacting a scaffold having a plurality of branches, wherein each of a plurality of branches terminates in a first reactive moiety, with a plurality of linking molecules, each linking molecule comprising a pharmacophore linked to a second reactive moiety, under conditions sufficient to induce a coupling reaction, such as a cycloaddition, between the first reactive moiety and the second reactive moiety. Thus, the first reactive moiety may comprise an optionally substituted alkene or alkyne (preferably an alkyne) and the second reactive moiety may comprise a diazoalkane, a nitrone, a nitrile oxide, an azide, or a nitrile imine (preferably a nitrile oxide or an azide). Alternatively, the first reactive moiety may comprise a diazoalkane, a nitrone, a nitrile oxide, an azide, or a nitrile imine (preferably a nitrile oxide or an azide) and the second reactive moiety may comprise an optionally substituted alkene or alkyne (preferably an alkyne). Similarly, one of the first and second reactive moieties may comprise a nucleophile and the other an electrophile, such that reaction between the nucleophile and electrophile forms a covalent bond.

In embodiments for preparing compounds with different pharmacophores, this method may be readily adapted by, for example:

1) contacting the scaffold (simultaneously or successively) with two or more linking molecules, wherein some linking molecules comprise a first pharmacophore and other linking molecules comprise a second pharmacophore, such that the linking molecules randomly react with the first reactive moieties (in this fashion the relative dispositions and even proportions of the different pharmacophores may differ from molecule to molecule); or 2) using a scaffold where some branches terminate with a first reactive moiety and other branches terminate with a second reactive moiety, and contacting the scaffold (simultaneously or successively) with a first linking molecule comprising a first pharmacophore linked to a third reactive moiety that selectively reacts with the first reactive moiety and a second linking molecule comprising a second pharmacophore linked to a fourth reactive moiety that selectively reacts with the second reactive moiety (for example, the first and third reactive moieties may comprise a nucleophile and an electrophile, while the second and fourth reactive moieties may undergo a [3+2] cycloaddition with each other).

In certain embodiments, compounds of the invention may have one or more chiral centers, whether in the pharmacophore, the scaffold, or the branches. In certain such embodiments, compounds of the invention may be enriched in one or more diastereomers or one or more enantiomers. For example, a compound of the invention may have greater than 30% de, 40% de, 50% de, 60% de, 70% de, 80% de, 90% de, or even 95% or greater de. A diastereo-enriched composition or mixture may comprise, for example, at least 60 mol percent of one diastereomer, or more preferably at least 75, 90, 95, or even 99 mol percent. In certain embodiments, the compound enriched in one diastereomer is substantially free of the other diastereomers, wherein substantially free means that the other diastereomers make up less than 10%, or less than 5%, or less than 4%, or less than 3%, or less than 2%, or less than 1% as compared to the amount of the primary diastereomer, e.g., in the composition or compound mixture. For example, if a composition or compound mixture contains 98 grams of a first diastereomer and 2 grams of a second diastereomer, it would be said to contain 98 mol percent of the first diastereomer and only 2% of the second diastereomer. In certain embodiments, a compound of the invention may have greater than 30% ee, 40% ee, 50% ee, 60% ee, 70% ee, 80% ee, 90% ee, or even 95% or greater ee. An enantio-enriched composition or mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the other enantiomer makes up less than 10%, or less than 5%, or less than 4%, or less than 3%, or less than 2%, or less than 1% as compared to the amount of the primary enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer. The compounds of the invention may also be racemic mixtures of enantiomers.

Compounds of any of the structures described herein and any composition of these compounds may be used in the manufacture of medicaments for the treatment of any diseases or conditions disclosed herein.

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x\text{-}y}$" when used in conjunction with a chemical moiety, such as, acyl, acyloxy, alkyl, alkenyl, alkynyl, or alkoxy is meant to include groups that contain from x to y carbons in the chain. For example, the term "$C_{x\text{-}y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2\text{-}y}$alkenyl" and "$C_{2\text{-}y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

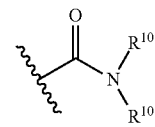

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof. e.g., a moiety that can be represented by

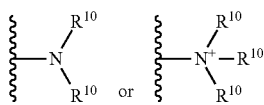

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

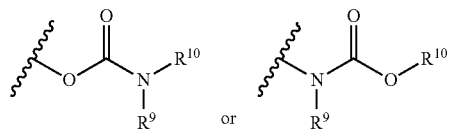

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

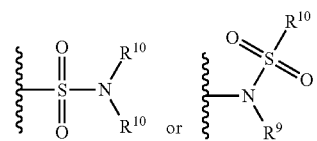

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

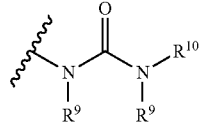

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996. John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "healthcare providers" refers to individuals or organizations that provide healthcare services to a person, community, etc. Examples of "healthcare providers" include doctors, hospitals, continuing care retirement communities, skilled nursing facilities, subacute care facilities, clinics, multispecialty clinics, freestanding ambulatory centers, home health agencies, and HMO's.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it as administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

The term "masking moiety" as used herein, refers to the chemical moiety that is a covalently bound modification of a pharmacophore that renders the compounds of the present invention to which it is attached prodrugs. A masking moiety is cleavable under, for example, acidic conditions, basic conditions, or physiologic conditions. When the masking moiety is cleaved, the prodrugs are converted to the therapeutically active agents of the present invention. Esters and carbonates can be used to mask hydroxyls, carbamates and amides can be used to mask amines, carboxyls can be masked as esters, etc., and in certain embodiments the precise masking moiety can be selected to be cleaved under conditions particular to a region of the digestive tract. For example, an amine or hydroxyl can be acylated by a 4-aminobutanoyl group, to form a prodrug that can be administered as a salt of the amine. In the acidic conditions of the stomach, the amino group will remain protonated, masking its nucleophilicity. In the more basic conditions of the small intestines, the ammonium group will be deprotonated, revealing the nucleophilic amine, which can nucleophilicly attack the amide or ester formed by the butanoyl group, ultimately revealing the amide or ester with the concomitant release of the protecting group as a lactam.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive mutes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use.

These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for administration to the mouth may be presented as a mouthwash, or an oral spray, or an oral ointment.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations which are suitable for vaginal administration also include pessaries, tampons, creams, gels, pastes, foams or spray formulations containing such carriers as are known in the art to be appropriate.

Alternatively or additionally, compositions can be formulated for delivery via a catheter, stent, wire, or other intraluminal device. Delivery via such devices may be especially useful for delivery to the bladder, urethra, ureter, rectum, or intestine.

Dosage forms for the topical administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benethamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

In certain embodiments, the invention relates to a method for conducting a pharmaceutical business, by manufacturing a formulation of a compound of the invention, or a kit as described herein, and marketing to healthcare providers the benefits of using the formulation or kit for treating or preventing any of the diseases or conditions as described herein.

In certain embodiments, the invention relates to a method for conducting a pharmaceutical business, by providing a distribution network for selling a formulation of a compound of the invention, or kit as described herein, and providing instruction material to patients or physicians for using the formulation for treating or preventing any of the diseases or conditions as described herein.

In certain embodiments, the invention comprises a method for conducting a pharmaceutical business, by determining an appropriate formulation and dosage of a compound of the invention for treating or preventing any of the diseases or conditions as described herein, conducting therapeutic profiling of identified formulations for efficacy and toxicity in animals, and providing a distribution network for selling an identified preparation as having an acceptable therapeutic profile. In certain embodiments, the method further includes providing a sales group for marketing the preparation to healthcare providers.

In certain embodiments, the invention relates to a method for conducting a pharmaceutical business by determining an appropriate formulation and dosage of a compound of the invention for treating or preventing any of the disease or conditions as described herein, and licensing, to a third party, the rights for further development and sale of the formulation.

EXAMPLES

Overview of Synitivity Platform™ Technology

Based upon the in viva disease model data obtained, the platform described herein allows oral administration, imparts gut-restriction, and provides access to a multi-mediator approach to the treatment of metabolic diseases. Furthermore, the platform allows introduction of precisely defined ratios of one to four distinct pharmacologically active agents suitable for oral delivery and imparts and maintains gut-restriction.

Gut-restriction provides a means to utilize validated molecular targets, which have failed by virtue of undesired toxicity associated with the expression of the specific molecular target in cell-types in tissue, organs, or organ systems not associated with disease treatment. Thus, gut-restriction of the pharmacologically active agent via this approach allows one to "re-purpose" (1) agents previously deemed "undesired" by virtue of toxicity unrelated to the disease-modifying mode of action, and also (2) those molecular targets that demonstrate a disease treatment utility and concomitant toxicity-related pharmacology in cells, tissue, organs, or organ systems unrelated to disease treatment. Lastly, as relates to potential for the re-purposing and clinical development of previously disclosed pharmacologically active agents, the gut-restriction platform described herein and drug discovery approach also provides a means to re-purpose existing drugs, as well as those molecules demonstrating clinical efficacy with undesired toxicity/safety pharmacology signals.

Specifically, with respect to the general IBD indication, namely, Crohn's and ulcerative colitis patient populations, the gut-restriction approach outlined herein is applicable to drug-naïve patient populations. The platform may also be applied in combination therapy via its addition to presently prescribed agents in patient populations utilizing existing agents. A significant feature of the drug platform described herein is that it is uniquely applicable to IBD patient populations either refractory to, or unresponsive to, any agent, whether administered orally or rectally, that is operative via an anti-inflammatory mode of action [e.g., a drug from steroid class of drugs prescribed for IBD], antibodies to the receptors of a range of pro-inflammatory cytokines, including but not limited to, IL-1beta, IL-6, TNF-alpha, as well as antibodies to those pro-inflammatory cytokines, per se.

The agents described herein agonize or antagonize the molecular target. The agent's required mode of action (e.g., agonization or antagonization) is specifically determined by the nature of the molecular target selected. The molecular target is specified intrinsically, with the platform acting via an orthosteric or allosteric mode of action to a wide range of known nutrient-sensing gut lumen-expressed, lamina propria-expressed molecular targets. In animal disease model experiments generally accepted to be predictive of outcomes in humans, the molecules described herein demonstrate dose-responsive lowering of pro-inflammatory cytokines in circulation and directly in gut mucosal cells. More specifically, the compounds of the gut-restricted drug discovery platform disclosed herein demonstrate reduction of IL-1beta levels in samples of rodent gut-microbiota. For example, in the rodent TNBS/DSS-induced colitis model, the orally administered gut-restricted compounds of the invention demonstrated dose responsive and statistically significant reductions in IL-1beta, IL-6, TNF-alpha, as well as improved mucosal healing determined by scoring gross morphology.

Another application of the gut-restricted drug discovery platform disclosed herein is for the treatment of cancers localized to various regions of the GI-tract driven by underlying gut-localized inflammation. An exemplary cancer is colorectal cancer, which can be modeled in rodents utilizing a variant of the DSS-induced colitis model. A gut-restricted compound, structurally unrelated to compounds useful for treating metabolic disease, was recognized by a specific gut lumen-expressed, lamina propria-expressed receptor, and demonstrated dose-responsive effects in vivo in the colorectal cancer variant of the DSS-induced colitis rodent disease model.

Applicability of Selected Molecular Targets to IBD
Structural Characteristics of the Agents Designed for Use in the Synitivity Platform [See FIG. 1].

There are a range of preferred qualities exhibited by the pharmacophores applied to the gut-restriction drug discovery Synitivity Platform described herein. The platform accommodates a wide range of pharmacological agents. For example, novel NCEs, re-purposed known clinical candidates, designed and biologically profiled small molecules, re-purposed new chemical entities, as well as re-purposed known drugs affecting gut lumen-expressed, lamina propria-expressed molecular targets can be utilized with the platform described herein.

The synthetic approach described herein utilizes unique modifications to known techniques. This modified methodology is designed to allow ready access to the wide range of elaborated matrix/dendrimer compounds described herein. For example, the synthetic routes to various gut-restriction platforms are convergent, in that the routes utilize a "polyyne" synthesis that affords a tetra-triazole dendrimer and provides access to different linker chain lengths. Features such as linker chain length, atom identity, and atom hybridization state contribute to the underlying conformations most necessary for the designed pharmacological agent's observed intrinsic potency, its in vivo disease model activity, and the imposed gut-restriction quality.

Although there is no intrinsic limitation to the nature of the linkers selected, in certain embodiments, preferred linkages include ether, amine, sulfide, and sulfoxide groups. In certain embodiments, the sulfoxide is chiral at the sulfur atom center, or achiral at the sulfur atom center. Further N-aryl or N,N-alkyl amides are acceptable linkers.

Materials

The following reagents are commercially available or were synthesized from reported procedures, as follows.

8-azido-3,6-dioxa-1-octanol was purchased from FutureChem Company, LTD., or was synthesized according to *Chem. Comm.* 2005, 34, 4315. Reagents 1-azido-3,6,9-trioxa-1-undecanol and 14-azido-3,6,9,12-tetraoxa-1-tetradecanol, mesylate reagents 8-azido-3,6-dioxa-1-octanol mesylate, 11-azido-3,6,9-trioxa-1-undecanol mesylate, and 1-N-tBoc-amino-3,6-dioxa-8-octanol mesylate, amino azide reagents 1-amino-8-azido-3,6-dioxaoctane and 1-amino-11-azido-3,6,9-trioxaundecane were also either purchased from FutureChem Company, LTD., or else synthesized according to known procedures. 5-azido-3-oxa-1-pentanol tosylate was prepared according to the procedure found in U.S. patent application publication 2013/0216475.

The following indole-derived carboxaldehydes were used in the invention and are commercially available: 1H-indole-3-carboxaldehyde, 5-chloro-1H-indole-3-carboxaldehyde, 1-(4-chlorobenzyloxy)-indole-3-carboxaldehyde, 1-benzyloxy-indole-3-carboxaldehyde, 1-phenylsulfonyl-indole-3-carboxaldehyde, and 1-benzyl-indole-3-carboxaldehyde.

The copper-based reagents, catalysts, and copper affinity purification reagents (e.g., Cuprisorb) utilized in the experimental section are commercially available.

TBTA (Tris-[(1-benzyl-1H-1,2,3-triazol-4-yl)methyl] amine, also known as tris-(benzyltriazolylmethyl)amine), a stabilizing ligand for Cu(I), was synthesized according to a known procedure in 40% yield (see Lewis, et al., *J. Am. Chem. Soc.* 2004, 126, 9152-3).

General Synthetic Methods

Incorporation of Pharmacological Agent Via Dendrimer/Azide Side-Chain Synthesis

Etherification introduces the "pharmacological agent" and provides access to variable chain-length polyether and azide precursors. The installation of heteroatoms can be completed in a flexible synthetic manner via Mitsunobu reaction and variants (Schemes 2 and 3). Typically, no matter the relative molecular complexity of the side chain one may select, a Mitsunobu variant is usually a compatible reaction. Thus, the conversion to the azide provides a dendrimer "side-chain" precursor suitable for use in "click" cycloaddition.

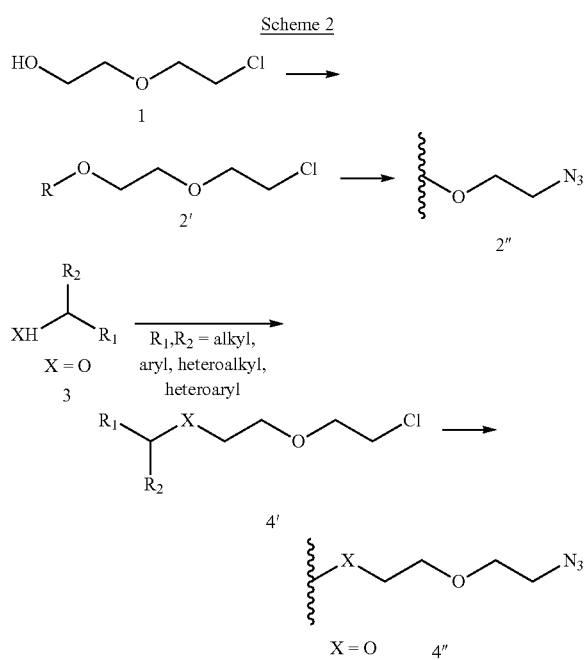

Scheme 2

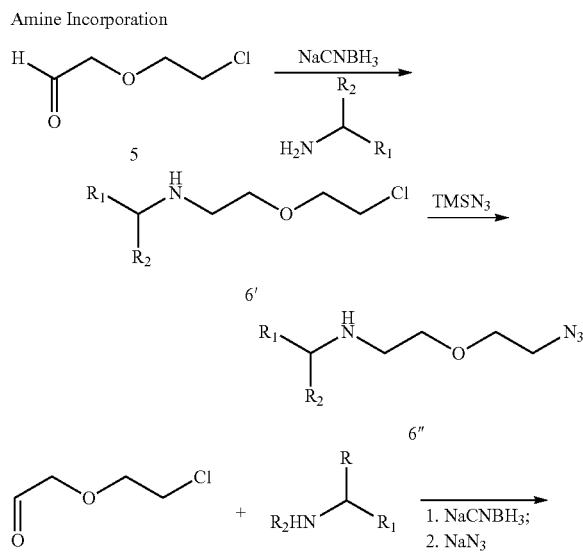

Scheme 3
Amine Incorporation

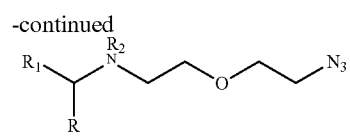

Synthetic Methods

1. Synthesis of Acetylene-Substituted Amino Reagents
   i. Synthesis of N,N,N',N'-Tetrapropargyl Ethylene Diamine (1)

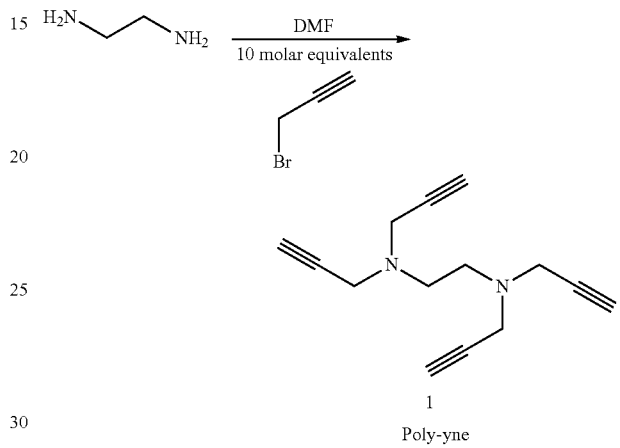

Poly-yne

The tetra-substituted ethylene diamine was prepared as reported in EP 0 431 700 B1. Specifically, into a reaction vessel fitted with a stirrer, a reflux condenser and a nitrogen gas inlet tube, were placed ethylene diamine (30.05 g, 0.5 mol), sodium hydroxide (84.21 g), deionized water (180 g), methylene chloride (180 g) and tetrabutyl-ammonium bromide (1.0 g) and the mixture was stirred and propargyl bromide (249.81 g, 2.1 mol) was added dropwise at room temperature. After complete addition, the mixture was heated to 50° C. and maintained at 50° C. for 6 hours. Thereafter, the mixture was allowed to cool to room temperature, the methylene chloride layer separated, washed with deionized water (3×), dried of anhydrous sodium sulfate, filtered and concentrated at reduced pressure affording tetra-alkylated diamine. The product was subjected to silica gel column chromatography to obtain purified N,N,N',N'-tetrapropargyl ethylene diamine, 1 (92% yield).

ii. Synthesis of Triethanolamino-Tripropargyl Ether (2) Via Etherification of Triethanolamine To an anhydrous THF (15 mL) solution of triethanolamine (1.4 mmol) was added NaH (100.80 mg, 4.2 mmol) at 0° C. and the resulting mixture was maintained at 0° C. for 20 minutes. A catalytic amount (0.42 mmol) of tetrabutylammonium iodide (TBAI) was added in one portion followed by rapid, dropwise addition of propargyl bromide (1.3 mL, 14.4 mmol) over 60 seconds. The mixture was warmed to room temperature and stirred at room temperature for an additional 18 h. The reaction was quenched by addition of ice cold distilled water (20 mL), the resulting mixture allowed to stir for 15 min, methylene chloride (40 mL) was then added and the pH adjusted to pH=2.0 via addition of aqueous 1N HCl. The layers were separated and the aqueous layer was extracted (2×) with methylene chloride (15 mL). The aqueous layer was then added to methylene chloride (25 mL), the pH adjusted to pH=9.5 by addition of 2N NaOH and the layers were separated. The aqueous layer was extracted with methylene chloride (2×20 mL), the organic layers combined, dried over anhydrous sodium sulfate and concentrated at reduced pressure affording the desired tripropargyl ether (1) used without further purification (81% mass balance). Mass spec: HRMS calc'd: $C_{15}H_{21}NO_3$, 263.3321; found: 263.3302; M+1 264.1556.

2. Synthesis of 1N-Substituted Indole-3-Carboxaldehyde Intermediates

Exemplary synthetic procedures for the N-functionalization of indole derivatives may be found in Vartale et al., *Int J Pharm Pharm Sci*, 2012, Vol 4, Suppl 4, 635-641.

ii. Representative Procedure for the Conversion of 1H-Indole-3-Carboxaldehyde into the Corresponding 1-Phenyl-3-Carboxaldehyde (3)

$Cs_2CO_3$ (2 mmol) was heated to 130° C. under $N_2$. After 24 h the mixture was allowed to warm to room temperature and diluted with EtOAc (10 mL). The solids removed by filtering through a bed of celite:cuprisorb (1:1), the filtrate washed with water (2×5 mL) and the organic layer concentrated under reduced pressure. The residue was added to water: ethyl acetate (1:1, 20 mL), the pH adjusted to pH=5.5, the layers separated, and the ethyl acetate layer added to an equal volume of distilled water. The pH of the ethyl acetate/water mixture was adjusted to pH=9 by addition of aqueous 2N NaOH, the layers separated, the aqueous layer extracted with an equal volume of methylene chloride (2×), the ethyl acetate and methylene chloride extracts were combined, dried over anhydrous sodium sulfate and concentrated at reduced pressure to afford 1-phenyl-indole-3 carboxaldehyde (3) 47% yield. Mass spec: HRMS calc'd: $C_{15}H_{11}NO$, 221.2539; found: 221.0841; 222.0802.

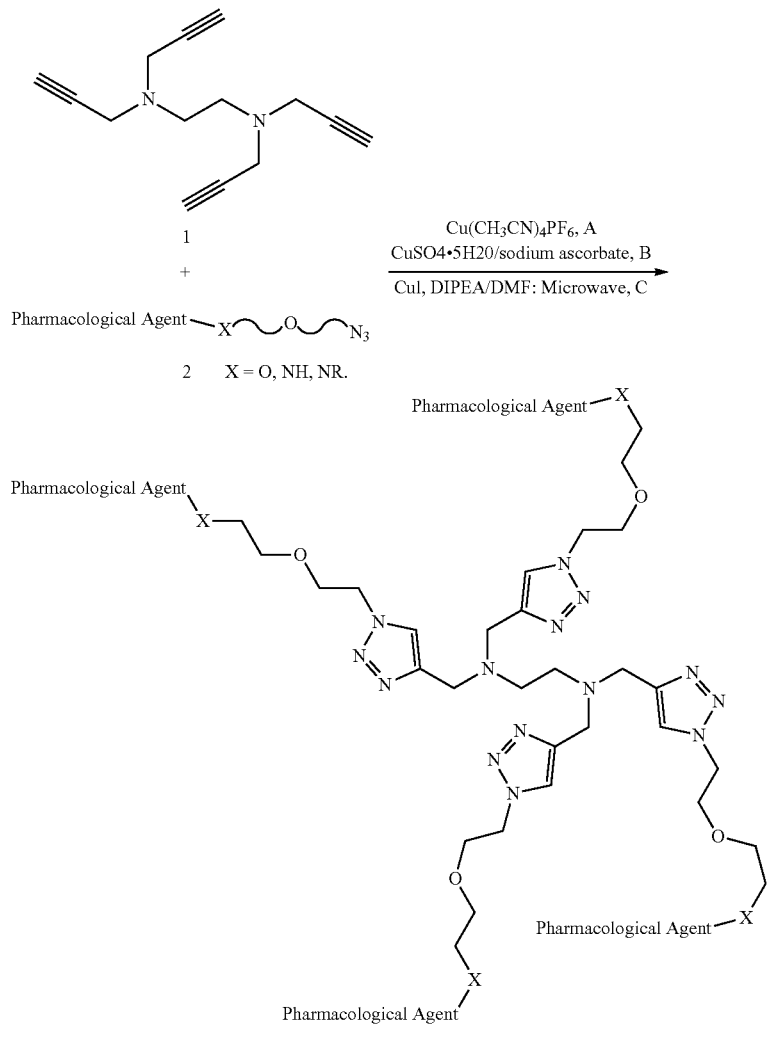

Reaction Conditions: i. Room temperature/methylene chloride A and B; ii. 0.2 to 1.0 equivalents of reagent A, B, or C; iii. CuprisorbTM resin. iv. Yields 70-90% intermediate 3 was synthesized utilizing the procedure reported in Hu, L. et al. *Tetrahedron* 2014, 70, 5626-5631. Specifically, an anhydrous DMF (2 mL) solution of 1H-indole-3-carboxaldehyde (1 mmol), phenyl iodide (1.5 mmol), CuI (0.1 mmol), metformin hydrochloride (0.2 mmol), and ii. Representative Procedure for the Conversion of 1H-Indole-3-Carboxaldehyde into the Corresponding 1-Phenyl Sulfonyl-Indole-3-Carboxaldehyde (4)

A solution of 1H-indole-3-carboxaldehyde (1.26 mmol) in methylene chloride (4.5 mL), TEA (0.26 g, 2.5 mmol), DMAP (15 mg, 0.13 mmol) and phenyl sulfonyl chloride (1.3 mmol) was stirred at room temperature overnight. An equal volume of water then was added, the pH1 adjusted to pH=2.5 by addition of 1N aqueous HC, the layers separated, the organic layer added to an equal volume of fresh water, the pH adjusted to pH=9, by addition of 1N aqueous NaOH, the layers separated, the aqueous layer extracted (2×) with an equal volume of methylene chloride, the methylene chloride extracts combined, dried over anhydrous sodium sulfate, filtered, and concentrated under vacuum to afford the 1-phenyl sulfonyl-indole-3 carboxaldehyde (4) (65% mass balance) used without further purification. Mass spec: HRMS calc'd: $C_{15}H_{11}NO_3S$, 285.3177; found: 285.0460.

iii. Representative Procedure for the Conversion of 1H-Indole-3-Carboxaldehyde into the Corresponding 1-Benzyloxy-Indole-3-Carboxaldehyde (5)

A solution of 1H-indole-3-carboxaldehyde (1.26 mmol) in methylene chloride (4.5 ml), TEA (0.26 g, 2.5 mmol), DMAP (15 mg, 0.13 mmol) and benzyloxy chloride (1.3 mmol) was stirred at room temperature overnight. An equal volume of water then was added, the pH adjusted to pH=2.5 by addition of 1N aqueous HCl, the layers separated, the aqueous layer extracted (1×) with an equal volume of methylene chloride, the organic layers combined, added to an equal volume of fresh water, the pH adjusted to pH=9, by addition of 1N aqueous NaOH, the layers separated, the aqueous layer extracted (2×) with an equal volume of methylene chloride, the methylene chloride extracts combined, dried over anhydrous sodium sulfate, filtered, and concentrated under vacuum to afford 1-benzyloxy-indole-3 carboxaldehyde (5) (72% mass balance) used without further purification. Mass spec: HRMS calc'd: $C_{16}H_{11}NO_2$, 249.2640; found: 249.0790.

(5a): 1-(4-chloro-benzyloxy)-indole-3-carboxaldehyde was also made according to the procedure, above; (86% mass balance) used without further purification. Mass spec: HRMS calc'd: $C_{16}H_{10}ClNO_2$, 283.0400; found: 283.0497.

iv. Representative Procedure for the Conversion of 5-Chloro-1H-Indole-3-Carboxaldehyde into the Corresponding 5-Chloro-1-Phenyl Sulfonyl-Indole-3-Carboxaldehyde (6)

A solution of 5-chloro-1H-indole-3-carboxaldehyde (1.26 mmol) in methylene chloride (4.5 ml), TEA (0.26 g, 2.5 mmol), DMAP (15 mg, 0.13 mmol) and phenyl sulfonyl chloride (1.3 mmol) was stirred at room temperature overnight. An equal volume of water then was added, the pH adjusted to pH=2.5 by addition of 1N aqueous HCl, the layers separated, the aqueous layer extracted (1×) with an equal volume of methylene chloride, the organic layers combined, added to an equal volume of fresh water, the pH adjusted to pH=9, by addition of 1N aqueous NaOH, the layers separated, the aqueous layer extracted (2×) with an equal volume of methylene chloride, the methylene chloride extracts combined, dried over anhydrous sodium sulfate, filtered, and concentrated under vacuum to afford 5-chloro-(1-phenylsulfonyl)-indole-3-carboxaldehyde (6) (55% mass balance) used without further purification. Mass spec: HRMS calc'd: $C_{15}H_{10}NO_3S$, 319.7627; found: 319.0070; 321.0028.

v. Representative Procedure for the Conversion of 5-Chloro-1H-Indole-3-Carboxaldehyde into the Corresponding 5-Chloro-(1-Benzyloxy)-Indole-3-Carboxaldehyde (7)

A solution of 5-chloro-1H-indole-3-carboxaldehyde (1.26 mmol) in methylene chloride (4.5 ml), TEA (0.26 g, 2.5 mmol), DMAP (15 mg, 0.13 mmol) and benzyloxy chloride (1.3 mmol) was stirred at room temperature overnight. An equal volume of water then was added, the pH adjusted to pH=2.5 by addition of 1N aqueous HCl, the layers separated, the aqueous layer extracted (1×) with an equal volume of methylene chloride, the organic layers combined, added to an equal volume of fresh water, the pH adjusted to pH=9, by addition of 1N aqueous NaOH, the layers separated, the aqueous layer extracted (2×) with an equal volume of methylene chloride, the methane chloride extracts combined, dried over anhydrous sodium sulfate, filtered, and concentrated under vacuum to afford 5-chloro-(1-benzyloxy)-indole-3 carboxaldehyde (7) (80% mass balance) used without further purification. Mass spec: HRMS calc'd: $C_{16}H_{10}ClNO_2$, 283.7090; found: 283.0400; 285.0371.

(7a): 5-chloro-1-(4-chloro-benzyloxy)-indole-3-carboxaldehyde; (93% mass balance) used without further purification. Mass spec: HRMS calc'd: $C_{16}H_9Cl_2NO_2$, 317.0009; found: 317.0045; 318.9108.

3. Synthesis of 1N-Substituted Indole-3-Methylenehydroxy Intermediates and their Conversion into Pegylated Azido Ethers i. Representative Procedure for the Conversion of 1-Substituted-Indole-3-Carboxaldehydes into their Corresponding 1-Substituted Indole-3-Methylenehydroxy Carbinol Derivatives To a methanol/THF (1:1, 20 mL) solution of 5-chloro-1-(4-chloro-benzyloxy)-indole-3-carbaldehyde, 7a. (0.75 mmol) maintained at 0° C. was slowly added NaBH$_4$ (32 mg, 0.825 mmol). After addition is complete, the reaction, maintained at 0° C., is allowed to stir for additional 30 minutes and then allowed to warm to room temperature. Reaction progress was assessed by thin layer chromatography (tlc) [silica plate; $CH_2Cl_2$:Helexane:MeOH (90:9:1)] and, upon indication of total consumption of the indole-3-carboxaldehyde, 10 ml of 1N HCl was added, the methanol/THF was removed under reduced pressure, and fresh water (20 ml) was added to the resulting residue, which was extracted with ethyl acetate (3×10 ml). The combined organic extracts were washed with water, 10% NaHCO$_3$, brine, dried over anhydrous sodium sulfate, filtered and concentrated. The residue was purified by flash chromatography (silica) affording 5-chloro-1-(4-chloro-benzyloxy)-indole-3-methylenehydroxy carbinol (1) (85% yield). Mass spec: HRMS calc'd: $C_{16}H_{11}Cl_2NO_2$, 319.0167; found: 319.0162; 321.0136; 323.0107.

The following substrates were made according to the representative procedure, above.

(8a): 5-chloro-1-(benzyloxy)-indole-3-methylenehydroxy carbinol; (79% yield); Mass spec: HRMS calc'd: $C_{16}H_{12}ClNO_2$, 285.0556; found: 285.0498; 287.0527.

(8b): 1-benzyloxy-indole-3-methylenehydroxy carbinol; (90% yield); Mass spec: HRMS calc'd: $C_{16}H_{13}NO_2$, 251.0947; found: 251.0915.

(8c): 5-chloro-(1-phenylsulfonyl)-indole-3-methylenehydroxy carbinol; (80% yield); Mass spec: HRMS calc'd: $C_{15}H_{12}ClNO_3S$, 321.0226; found: 321.0216; 323.0197.

(8d): 1-phenylsulfonyl-indole-3-methylenehydroxy carbinol; (80% yield); Mass spec: HRMS calc'd: $C_{15}H_{12}NO_3S$, 287.0616; found: 287.0686.

(8e): 1-phenyl-indole-3-methylenehydroxy carbinol; (97% yield); Mass spec: HRMS calc'd: $C_{15}H_{13}NO$, 223.0997; found: 223.0957.

(8f): 1-(4-chloro-benzyloxy)-indole-3-methylenehydroxy carbinol; (84% yield); Mass spec: HRMS calc'd: $C_{16}H_{12}ClNO_2$, 285.0556; found: 285.0517; 287.0527.

ii. Representative Procedure for the Conversion of 1-Substituted-Indole-3 Methylenehydroxy Carbinols into their Corresponding 1-Substituted Indole-3 Methylenehydroxy-Pegylated Azido Ether Derivatives Via Azido-Tosylate PEG-Reagents.

To an anhydrous THF/DMF (4:1, 15 mL) solution of 5-chloro-(4-chloro-benzyloxy)-indole-3-methylenehydroxy carbinol [(8), 446 mg, 1.4 mmol] was added NaH (33.6 mg, 1.4 mmol) at 0° C., and the resulting reaction mixture maintained at 0° C. for 20 minutes. To the THF/DMF solution maintained at 0° C. was added tetrabutylammonium iodide (TBAI) (0.03 mmol) in one portion, followed by drop-wise addition of an anhydrous THF/DMF (4:1, 7 mL) solution of 5-azido-3-oxa-1-pentanol tosylate (420 mg, 1.4 mmol). After completion of the tosylate addition, the mixture was allowed to warm to room temperature and maintained at room temperature for 10 h. The reaction was quenched by addition of ice cold water (20 mL), the resulting mixture allowed to stir for 15 min, methylene chloride (30 mL) added, and the pH adjusted to pH=2.0 via addition of aqueous 1N HCl. The layers were separated and the aqueous layer extracted with fresh methylene chloride (2×10 mL). The combined methylene chloride layers were added to freshly distilled water (20 mL), the pH adjusted to pH=9.5 by addition of aqueous 2N NaOH and the layers separated. The aqueous layer was extracted with fresh methylene chloride (2×8 mL), the methylene chloride fractions combined, dried over anhydrous sodium sulfate, concentrated at reduced pressure, and isolated by filtration through silica gel eluted with methylene chloride to afford the desired 5-chloro-(4-chloro-benzyloxy)-indole-3-methylene-oxa-azido ether (9) (70% yield). Mass spec: HRMS calc'd: $C_{20}H_{18}Cl_2N_4O_3$, 432.0756; found: 432.0754; 434.0724.

(9a): 5-chloro-1-(benzyloxy)-indole-3-methylene-oxa-azido ether, (76% yield); Mass spec: HRMS calc'd: $C_{20}H_{19}ClN_4O_3$, 398.1146; found: 398.1108; 400.1118.

(9b): 1-Benzyloxy-indole-3-Methylene-oxa-azido ether; (91% yield); Mass spec: HRMS calc'd: $C_{20}H_{20}N_4O_3$, 364.1535; found: 364.1569.

(9c): 5-chloro-(1-phenylsulfonyl)-indole-3-methylene-oxa-azido ether; (73% yield): Mass spec: HRMS calc'd: $C_{19}H_{19}ClN_4O_4S$, 434.0815; found: 434.0803; 436.0784.

(9d): 1-phenylsulfonyl-indole-3-methylene-oxa-azido ether; (62% yield): Mass spec: HRMS calc'd: $C_{19}H_{20}N_4O_4S$, 400.1205; found: 400.1191.

(9e): 1-phenyl-indole-3-methylene-oxa-azido ether; (90% yield): Mass spec: HRMS calc'd: $C_{19}H_{20}N_4O_2$, 336.1586; found: 336.1518.

(9f): 1-(4-chloro-benzyloxy)-indole-3-methylene-oxa-azido ether; (74% yield); Mass spec: HRMS calc'd: $C_{20}H_{19}ClN_4O_3$, 398.1146; found: 398.1098; 400.1106.

iii. Representative Procedure for the Conversion of 1-Substituted Indole-3-Methylenehydroxy Carbinols into their Corresponding 1-Substituted Indole-3-Methylenehydroxy-Pegylated Azido Ether Derivatives Via Azido-Mesylate PEG-Reagents.

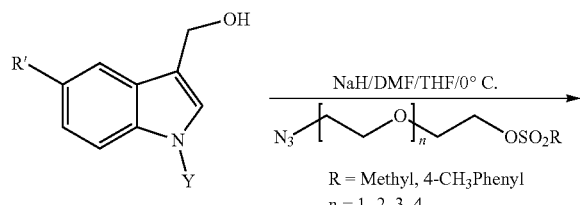

R' = H, Halogen, Alkyl, O-Alkyl
Y = Ph, CH$_2$Ph-R, COPh-R, SO$_2$Ph-4CH$_3$
R = Methyl, 4-CH$_3$Phenyl
n = 1, 2, 3, 4

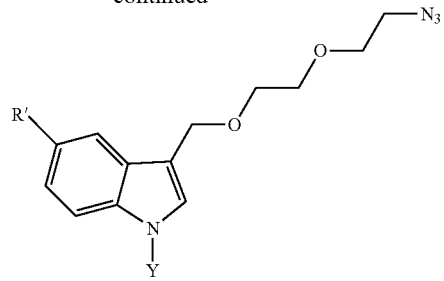

To an anhydrous THF/DMF (4:1, 5 mL) solution of 5-chloro-(4-chloro-benzyloxy)-indole-3-methylenehydroxy carbinol (446 mg, 1.4 mmol) was added NaH (33.6 mg, 1.4 mmol) at 0° C., the resulting mixture maintained at 0° C. for 20 minutes. To this mixture, maintained at 0° C., was added tetrabutylammonium iodide (TBAI) (0.014 mmol) in one portion, followed by drop wise addition of an anhydrous THF/DMF (4:1, 5 mL) solution of 8-azido-3,6-dioxa-1-octanol mesylate (354.2 mg, 1.4 mmol). After addition complete, the mixture was allowed to warm to room temperature and maintained at room temperature for 4.5 h. The reaction was quenched by addition of ice cold water (20 mL), the resulting mixture allowed to stir for 15 min, methylene chloride (30 mL) added, and the pH adjusted to pH=2.0 via addition of aqueous 1N HCl. The layers were separated and the aqueous layer extracted with fresh methylene chloride (2×10 mL). The combined methylene chloride layers were added to fresh water (20 mL), the pH adjusted to pH=9.5 by addition of aqueous 2N NaOH and the layers separated. The aqueous layer was extracted with fresh methylene chloride (2×8 mL), the methylene chloride fractions combined, dried over anhydrous sodium sulfate, concentrated at reduced pressure, and isolated by filtering through silica gel eluted with methylene chloride to afford the desired 5-chloro-(4-chloro-benzyloxy)-indole-3-methylene-oxa-azido ether (10) (80% yield). Mass spec: Mass spec: HRMS calc'd: $C_{22}H_{22}Cl_2N_4O_4$, 476.1018; found: 476.1015; 478.0986.

(10a): 5-chloro-1-(benzyloxy)-indole-3-methylene-oxa-azido ether; (83% yield); Mass spec: HRMS calc'd: $C_{22}H_{23}ClN_4O_4$, 442.1408; found: 442.1368; 444.1370.

(10b): 1-benzyloxy-indole-3-methylene-oxa-azido ether; (90% yield); Mass spec: HRMS calc'd: $C_{22}H_{24}N_4O_4$, 408.1797; found: 408.1691.

(10c): 5-chloro-(1-phenylsulfonyl)-indole-3-methylene-oxa-azido ether; (68% yield); Mass spec: HRMS calc'd: $C_{21}H_{23}ClN_4O_5S$, 478.1077; found: 478.0911; 480.1041.

(10d): 1-phenylsulfonyl-indole-3-methylene-oxa-azido ether; (65% yield); Mass spec: HRMS calc'd: $C_{21}H_{24}N_4O_5S$, 444.1467; found: 444.1423.

(10e): 1-phenyl-indole-3-methylene-oxa-azido ether; (85% yield); Mass spec: HRMS calc'd: $C_{21}H_{24}N_4O_3$, 380.01848; found: 380.1788.

(10f): 1-(4-chloro-benzyloxy)-indole-3-methylene-oxa-azido ether; (81% yield); Mass spec: HRMS calc'd: $C_{22}H_{23}ClN_4O_4$, 442.1408; found: 442.1372; 444.1346.

iv. Reaction of 1-Substituted Indole-3-Methylenehydroxy, Carbinols with Azido-Mesylate Reagents.

Substituted indole-3-methylene-oxa-azido ethers resulted from indole carbinol addition to the 11-azido-3,6,9-trioxa-1-undecanol mesylate reagents. Refer to Section 3.iii. for an analogous synthetic procedure.

(10g): 5-chloro-1-(4-chloro-benzyloxy)-indole-3-methylene-oxa-azido ether; (59% yield); Mass spec: HRMS calc'd: $C_{24}H_{26}Cl_2N_4O_5$, 520.1281; found: 520.1221; 522.1250.

(10h): 5-chloro-1(benzyloxy)-indol-3-methylene-oxa-azido ether; (83% yield); Mass spec: HRMS calc'd: $C_{24}H_{27}ClN_4O_5$, 486.1670; found: 486.1602; 488.1635.

(10i): 1-benzyloxy-indole-3-methylene-oxa-azido ether; (82% yield); Mass spec: HRMS calc'd: $C_{24}H_{28}N_4O_5$, 452.2059; found: 452.2003.

(10j): 5-chloro-(1-phenylsulfonyl)-indole-3-methylene-oxa-azido ether; (55% yield); Mass spec: HRMS calc'd: $C_{23}H_{27}ClN_4O_6S$, 522.1339; found: 522.1289; 524.1301.

(10k): 1-phenylsulfonyl-indole-3-methylene-oxa-azido ether; (43% yield); Mass spec: HRMS calc'd: $C_{23}H_{28}N_4O_6S$, 488.1729; found: 488.1647.

(10l): 1-phenyl-indole-3-methylene-oxa-azido ether; (91% yield), Mass spec: HRMS calc'd: $C_{23}H_{28}N_4O_4$, 424.2111; found: 424.2055.

(10m): 1-(4-chloro-benzyloxy)-indole-3-methylene-oxa-azido ether; (89% yield); Mass spec: HRMS calc'd: $C_{24}H_{27}ClN_4O_5$, 486.1670; found: 486.1614, 488.1593.

4. Synthesis of Gut-Restricted Dendrimers Utilizing the Copper Catalyzed [3+2] Huisgen Cycloaddition [CuAAC Reaction].

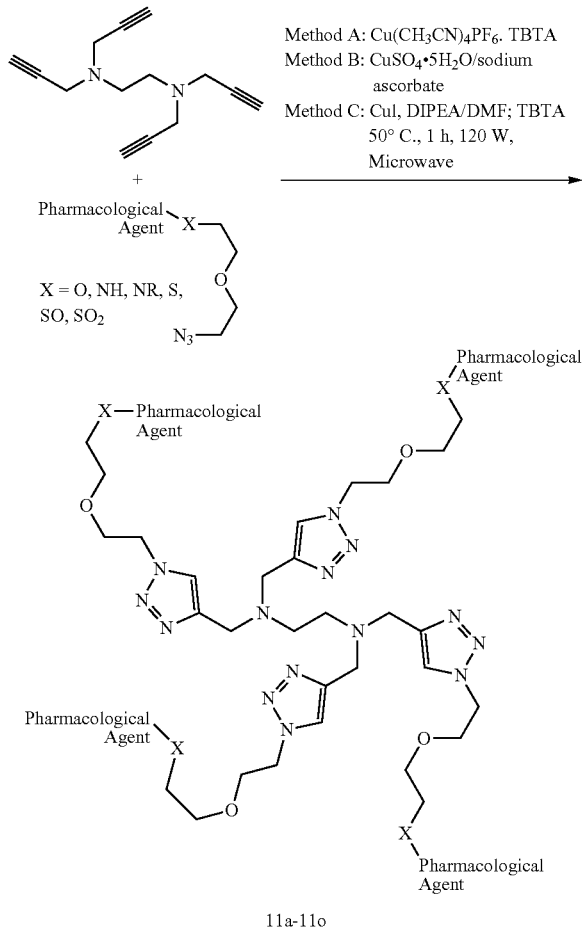

11a-11o i. Method A: General Procedure for a CuAAC Reaction Utilizing Tetrapropargyl Ethylenediamine and 1-Substituted Indole-3-Methylene-Oxa-Pegylated Azido Ethers, Affording Tetra-Triazole-Linked Cycloaddition Products A THF:DMF (2:1, 45 mL) solution of tetrapropargyl ethylenediamine (0.2 mmol) and a 1-substituted indole-3-methyleneoxa-pegylated azido ether (0.8 mmol) was treated with an 8M aqueous solution of $Cu(OAc)_2 \cdot H_2O$ (80 mL, 0.16 mmol), freshly prepared 8M aqueous solution of sodium ascorbate (160 mL, 0.32 mmol) and TBTA (15 mol %). The reaction mixture was allowed to stir at room temperature for 18 h, then diluted with EtOAc (180 mL), filtered through CupriSorb, the filtrates collected, added to an equal volume of water, the pH adjusted to pH=9, the layers separated, and the aqueous layer extracted with fresh methylene chloride (2×60 mL). The organic layers were combined, washed with brine (3×40) mL), dried over anhydrous $Na_2SO_4$, and concentrated under reduced pressure. This material was flash chromatographed on a C18-reverse phase column to provide the desired tetra-triazole ether.

Yield and the HR MS for Representative Examples:

(11a): 1-(benzyloxy)-indole-3-methyleneoxa-(3-oxa-pentyl)-tetra-triazole-ethylenediamine; (61% yield); Mass spec: HRMS calc'd: $C_{94}H_{96}N_{18}O_{12}$, 1668.7445; found: 1668.7434; 1669.7468.

(11b): 1-(4-chlorobenzyloxy)-indole-3-methyleneoxa-(3-oxa-pentyl)-tetra-triazole-ethylenediamine; (58% yield); Mass spec: HRMS calc'd: $C_{94}H_{92}Cl_4N_{18}O_{12}$, 1804.5887; found: 1804.5825; 1806.5848; 1807.5833; 1808.5798.

(11c): 5-chloro-1-(4-chlorobenzyloxy)-indole-3-methyleneoxa-(3-oxa-pentyl)-tetra-triazole-ethylenediamine; (74% yield): Mass spec: HRMS calc'd: $C_{94}H_{88}Cl_4N_{18}O_{12}$, 1940.4330; found: 1940.4290; 1944.4200; 1945.4292; 1947.4246.

(11d): 5-chloro-(1-benzyloxy)-indole-3-methyleneoxa-(3-oxa-pentyl)-tetra-triazole-ethylenediamine; (48% yield); Mass spec: HRMS calc'd: $C_{94}H_{92}Cl_4N_{18}O_{12}$, 1804.5887; found: 1804.5821; 1806.5202; 1807.5858.

(11e): 5-chloro-(1-phenylsulfonyl)-indole-3-methylene-oxa-(3-oxa-pentyl)-tetra-triazole-ethylenediamine; (80% yield); Mass spec: HRMS calc'd: $C_{90}H_{92}Cl_4N_{18}O_{16}S_4$, 1948.4562; found: 1948.4518; 1950.4568; 1951.4513.

ii. Method B: General Procedure of Microwave-Based CuAAC Reaction Utilizing Tetrapropargyl Ethylenediamine and 1-Substituted Indole-3-Methylene-Oxa-Pegylated Azido Ethers, Affording Tera-Triazole-Linked Cycloaddition Products A DMF solution of a 1-substituted indole 3-pegylated azido ether (4.4 equiv) and tetrapropargyl-ethylenediamine (1.1 equiv) was added to TBTA (15 mol %), $CuSO_4$ (20 mol %) and sodium ascorbate (30 mol %) and the resulting mixture heated to 50° C. in a 120 W microwave oven for 1 hr. The reaction mixture was allowed to cool to room temperature, then diluted with distilled water, EtOAc, and filtered through CupriSorb. The filtrates were collected, added to an equal volume of water, the pH adjusted to pH=9, the layers separated, and the aqueous layer extracted with fresh methylene chloride (2×60 mL). The organic layers were combined, washed with brine (3×40 mL), dried over anhydrous $Na_2SO_4$, and concentrated under reduced pressure. This material was flash chromatographed on a C18-reverse phase column to provide the desired tetra-triazole ether. Yield and the HR MS for representative examples:

(11a): 1-(benzyloxy)-indole-3-methyleneoxa-(3-oxa-pentyl)-tetratriazole-ethylenediamine (77% yield); Mass spec: HRMS calc'd: $C_{94}H_{96}N_{18}O_{12}$, 1668.7445; found: 1668.7404; 1669.7426.

(11f): 1-(benzyloxy)-indole-3-methyleneoxa-(3,6-dioxa-octyl)-tetratriazole-ethylenediamine; (64% yield); Mass spec: HRMS calc'd: $C_{102}H_{112}N_{18}O_{16}$, 1844.8489; found: 1844.8427; 1846.8546.

(11g): 1-(4-chlorobenzyloxy)-indole-3-methyleneoxa-(3,6-dioxa-octyl)-tetratriazole-ethylenediamine; (38% yield); Mass spec: HRMS calc'd: $C_{102}H_{105}Cl_4N_{18}O_{16}$, 1980.6931; found: 1980.6897; 1983.9686; 1984.6910.

(11h): 5-chloro-1-(4-chlorobenzyloxy)-indole-3-methyleneoxa-(3,6-dioxa-octyl)-tetratriazole-ethylenediamine: (81% yield); Mass spec: HRMS calc'd: $C_{102}H_{104}Cl_8N_{18}O_{16}$, 2116.5371; found: 2116.5311; 2121.5309; 2124.5314.

(11i): 5-chloro-(1-benzyloxy)-indole-3-methyleneoxa-(3,6-dioxa-octyl)-tetratriazole-ethylenediamine; (70% yield); Mass spec: HRMS calc'd: $C_{102}H_{108}Cl_4N_{18}O_{16}$, 1980.6931; found: 1980.6923; 1983.6898; 1984.6900.

(11j): 5-chloro-(1-phenylsulfonyl)-indole-3-methylene-oxa-(3,6-dioxa-octyl)-tetratriazole-ethylenediamine; (60% yield); Mass spec: HRMS calc'd: $C_{98}H_{108}Cl_4N_{18}O_{20}S_4$, 2124.5608; found: 2124.5600; 2126.5569; 2127.5615; 2128.5542.

iii. Method C: CuAAC Reaction Utilizing Tetrapropargyl Ethylenediamine and 1-Substituted Indole-3-Methylene-Oxa-Pegylated Azido Ethers, Affording Tetra-Triazole-Linked Cycloaddition Products An anhydrous acetonitrile (1.0 mL) solution of $Cu(MeCN)_4PF_6$ (7.5 mg, 0.08 mmol) was added via cannula to an anhydrous acetonitrile (1 mL) solution of tetrapropargyl-ethylenediamine (0.02 mmol), a 1-substituted indole-3-methylene-oxa-pegylated azide (0.08 mmol), 2,6-lutidine (10 uL, 0.08 mmol) and TBTA (8.0 mg, 0.016 mmol) that was maintained at 20° C. The resulting mixture was allowed to stir at room temperature for 24 hours, water was added (4 mL), the resulting mixture was slurried with CupriSorb and filtered through a celite/Cuprisorb mixture with additional methylene chloride. The filtrates were collected, added to an equal volume of water, the pH adjusted to pH=9, the layers were separated, and the aqueous layer was extracted with fresh methylene chloride (2×25 mL). The organic layers are combined, washed with brine (3×40 mL), dried over anhydrous $Na_2SO_4$, and concentrated under reduced pressure. The resulting material was flash chromatographed on a C18-reverse phase column to provide the desired tetra-triazole ether.

Yield and the HR MS for Representative Examples:

(11a): 1-(benzyloxy)-indole-3-Methyleneoxa-(3-oxa-pentyl)-tetratriazole-ethylenediamine; (70% yield); Mass spec: HRMS calc'd: $C_{94}H_{96}N_{18}O_{12}$, 1668.7445; found: 1668.7412; 1669.7438.

(11k): 1-(benzyloxy)-indole-3-methyleneoxa-(3,6,9-trioxa-undecyl)-tetratriazole-ethylenediamine; (78% yield); Mass spec: HRMS calc'd: $C_{110}H_{128}N_{18}O_{20}$, 2020.9535; found: 2020.9521; 2021.9554; 2022.9592; 2023.9622.

(11l): 1-(4-chlorobenzyloxy)-indole-3-methyleneoxa-(3,6,9-trioxa-undecyl)-tetratriazole-ethylenediamine; (72% yield), Mass spec: HRMS calc'd: $C_{110}H_{124}Cl_4N_{18}O_{20}$, 2156.7986: found: 2156.7922; 2159.7971, 2160.8025.

(11m): 5-chloro-1-(4-chlorobenzyloxy)-indole-3-methyleneoxa-(3,6,9-trioxa-undecyl)-tetratriazole-ethylenediamine; (70% yield); Mass spec: HRMS calc'd: $C_{110}H_{120}Cl_8N_{18}O_{20}$, 2292.6423; found: 2292.6465; 2297.6462; 2299.6395.

(11n): 5-chloro-(1-butyloxy)-indole-3-methyleneoxa-(3,6,9-trioxa-undecyl)-tetratriazole-ethylenediamine; (78% yield); Mass spec: HRMS calc'd: $C_{110}H_{124}Cl_4N_{18}O_{20}$, 2156.7986: found: 2156.7936; 2159.7900; 2160.8005.

(11o): 5-chloro-(1-phenylsulfonyl)-indole-3-methyleneoxa-(3,6,9-trioxa-undecyl)-tetratriazole-ethylenediamine; (63% yield); Mass spec: HRMS calc'd: $C_{106}H_{124}Cl_4N_{18}O_{24}S_4$, 2300.6667; found: 2300.6647; 2302.6619; 2303.6633; 2304.6647.

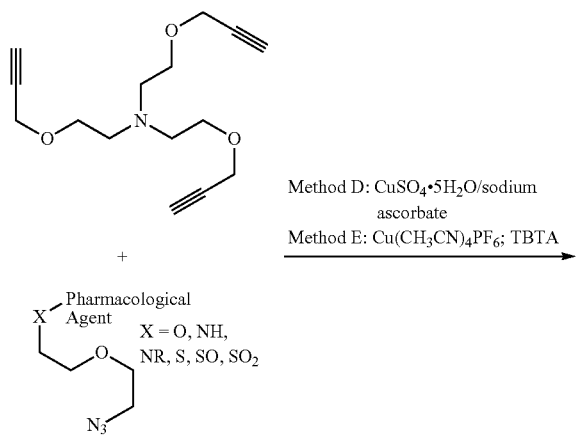

Method D: $CuSO_4 \cdot 5H_2O$/sodium ascorbate
Method E: $Cu(CH_3CN)_4PF_6$; TBTA

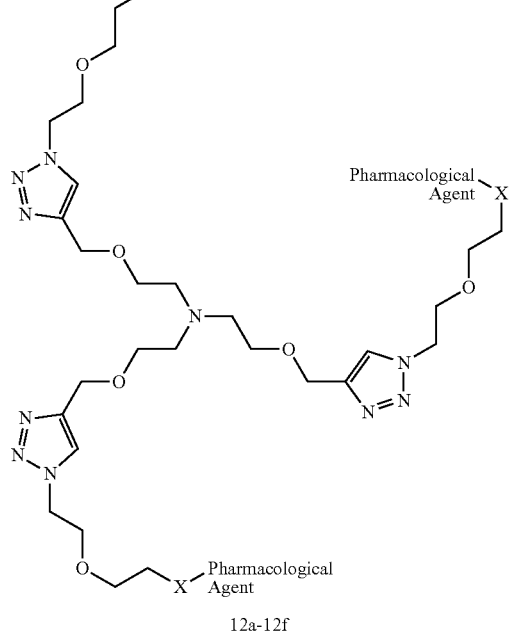

12a-12f iv. Method D: General Procedure for a CuAAC Reaction Utilizing Triethanolamino-Tripropargylether and 1-Substituted Indole-3-Methylene-Oxa-Pegylated Azido Ethers, Affording Tri-Triazole Linked Cycloaddition Products A THF:Acetonitrile (1:1, 45 mL) solution of tri-propargyl triethanolamino tri-ether (0.2 mmol) and 1-substituted indole-3-methylene-oxa-pegylated azido ether (0.6 mmol) is treated with an 8M aqueous solution of $Cu(OAc)_2 \cdot H_2O$ (80 mL, 0.16 mmol), freshly prepared KM aqueous solution of sodium ascorbate (160 mL, 0.32 mmol) and TBTA (15 mol %). The reaction mixture is allowed to stir at room temperature for 24 h, diluted with ethyl acetate (180 mL), and filtered through CupriSorb. Distilled water (50 mL) is added to the filtrate and the pH adjusted to pH=2 by addition of aqueous 1N HCl. The layers were separated and the aqueous layer extracted with methylene chloride (2×75 mL). The aqueous layer is then added to fresh ethyl acetate (100 mL), the pH adjusted to pH=9 by addition of aqueous 1N NaOH, and the layers separated. The aqueous layer is extracted with half its volume of methylene chloride (2×), all the organic extracts combined, dried over anhydrous sodium sulfate, filtered, concentrated at reduced pressure, and isolated by filtering through silica gel to afford the desired 1-substituted-indole-3-methylene-oxa-pegylated-triethanolamino tri-triazole ether.

In certain embodiments, the compound may be found in another layer during extraction due to the basicity of the compound. In such a case, the pH of the layers may be adjusted accordingly, and the compound may be collected from the desired layer.

Yield and the HR MS for Representative Examples:

12a: 1-(benzyloxy)-indole-3-methyleneoxa-(3-oxa-pentyl)-tri-triazole-(tri-(3-oxa)butyl)-1-amine; (81% yield); Mass spec: HRMS calc'd: $C_{75}H_{81}N_{13}O_{12}$, 1355.6121; found: 1355.6110; 1356.6144.

12b: 1-(benzyloxy)-indole-3-methyleneoxa-(3,6-dioxa-octyl)-tri-triazole-(tri-(3-oxa)butyl)-1-amine; (75% yield); Mass spec: HRMS calc'd: $C_{81}H_{93}N_{13}O_{15}$, 1487.6902; found: 1487.6895; 1488.6927; 1489.6980.

12c: 1-(benzyloxy)-indole-3-methyleneoxa-(3,6,9-trioxa-undecyl)-tri-triazole-(tri-(3-oxa)butyl)-1-amine; (75% yield); Mass spec: HRMS calc'd: $C_{87}H_{105}N_{13}O_{18}$, 1619.7687; found: 1619.7637; 1620.7702; 1621.7744; 1622.7718.

v. Method E: General Procedure for a CuAAC Reaction Utilizing Triethanolamino-Tripropargylether and 1-Substituted Indole-3-Methylene-Oxa-Pegylated Azido Ethers Affording Tri-Triazole Linked Cycloaddition Products An anhydrous acetonitrile (1 mL) solution of Cu(MeCN)$_4$PF$_6$ (0.06 mmol) was added via cannula to an anhydrous acetonitrile (1 mL) solution of tri-propargyl triethanolamino tri-ether (0.02 mmol), a 1-substituted indole-3-methylene-oxa-pegylated azide (0.06 mmol), 2,6-lutidine (10 uL, 0.08 mmol) and TBTA (6.0 mg, 0.012 mmol), maintained at 20° C. The resulting mixture was allowed to stir at room temperature for 24 hours, water was added (4 mL), the resulting mixture was slurried with CupriSorb and filtered through a celite/Cuprisorb mixture with additional methylene chloride. The filtrates were collected, added to an equal volume of water, the pH adjusted to pH=9, the layers separated, and the aqueous layer extracted with fresh methylene chloride (2×25 mL). The organic layers are combined, washed with brine (3×40 mL), dried over anhydrous Na$_2$SO$_4$, and concentrated under reduced pressure. The resulting material was flash chromatographed on a C18-reverse phase column to provide the desired tetra-triazole ether.

Yield and the HR MS for Representative Examples:

12a: 1-(benzyloxy)-indole-3-methyleneoxa-(3-oxa-pentyl)-tri-triazole-(tri-(3-oxa)butyl)-1-amine; (65% yield); Mass spec: HRMS calc'd: $C_{75}H_{81}N_{13}O_{12}$, 1355.6121; found: 1355.6090; 1356.6103.

12d: 5-chloro-1-(4-chlorobenzyloxy)-indole-3-methyleneoxa-(3-oxa-pentyl)-tri-triazole-(tri-(3-oxa)butyl)-1-amine; (65% yield); Mass spec: HRMS calc'd: $C_{75}H_{75}Cl_6N_{13}O_{12}$, 1559.3774; found: 1559.3712; 1561.3738; 1563.3705; 1565.3786.

12e: 5-chloro-1-(phenylsulfonyl)-indole-3-methyleneoxa-(3,6-dioxa-octyl)-Tri-triazole-(tri-(3-oxa)butyl)-1-amine; (80% yield); Mass spec: HRMS calc'd: $C_{78}H_{90}Cl_3N_{13}O_{18}S_3$, 1697.4741; found: 1697.4711; 1698.4704; 1699.4702; 1700.4702.

12f: 5-chloro-1-(phenylsulfonyl)-indole-3-methyleneoxa-(3,6,9-trioxa-undecyl)-tri-triazole-(tri-(3-oxa)butyl)-1-amine; (78% yield); Mass spec: HRMS calc'd: $C_{84}H_{102}Cl_3N_{13}O_{21}S_3$, 1829.5526; found: 1830.5551; 1831.5424; 1832.5518.

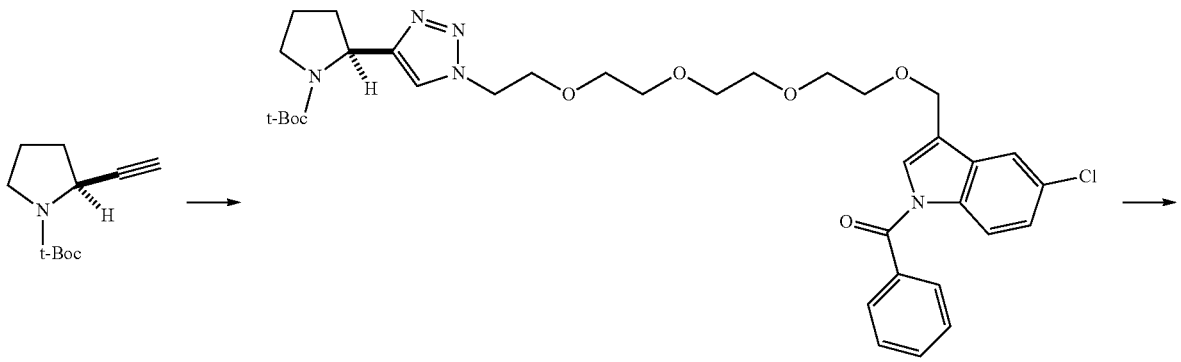

13

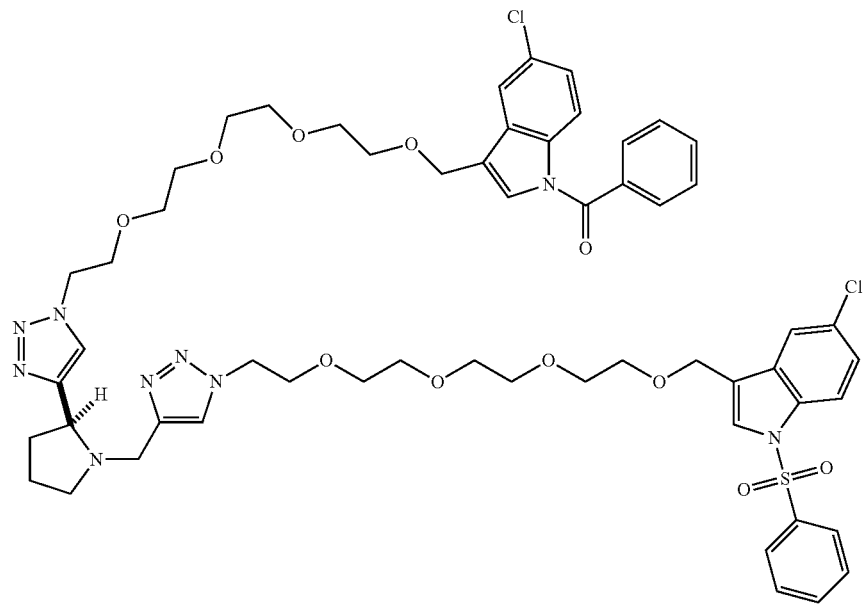

13a vi. Representative Procedure for a Huisgen [3+2] Cycloaddition Methodology Allowing Incorporation of Two Different Apes of Gut-Restricted Pharmacological Agents in a 1:1 Ratio in a Gut-Restricted Pegylated Dendrimer:

Synthesis of Compound (13a):

The known N-tBoc protected prolyl acetylene reagent (15) was prepared according to the procedure detailed in Tetrahedron Lett., 33, 3715 (1992). It was then utilized in the [3+2] cycloaddition reaction with azide 10h under reaction conditions described here as "Method C" affording 13: (95% mass yield); Mass spec: HRMS calc'd: $C_{35}H_{44}ClN_5O_7$, 681.2930; found: 681.2924; 682.2964; 683.2890; 684.2919.

Deprotection of t-Boc N-Prolyl-2-Triazole-3,6,9-Trioxa-Undecyl S-Chloro-1-Benzyloxy Indole Intermediate.

An ethyl acetate (10 mL) solution of N-tert-butyl carbamate-prolyl-2-substituted undecyl-triazole (0.32 mmol) pre-cooled to 0° C. was sparged with HCl gas for 1 min. The ice-bath was removed, the acidic solution allowed to warm to 23° C., and the mixture stirred for 2 h. The mixture was then concentrated to dryness to afford the de-protected intermediate 16 as its hydrochloride salt (98% mass yield), which was used without further purification.

Conversion of Intermediate 16 to 13a.

Intermediate 16 was first treated with propargylbromide affording the corresponding propargyl amine (17), as described in EP-O 431 700 B1, and used without further purification. Intermediate 17 was then utilized in the [3+2] cycloaddition reaction with the 5-chloro-1-phenylsulfonyl indole undecyl azide, (10j) under reaction conditions described here as "Method C" affording the desired, single dendrimer containing two different indole-3-pegylated triazole ethers, 5-chloro-(1-(benzyloxy)-indole-3-methylene-oxa-(3,6,9-oxa-undecyl)-triazole(2-propyl)-5-chloro-(1-(phenylsulfonyl)-indole-3-methyleneoxa-(3,6,9-oxa-undecyl)-triazole(1-prolyl) di-triazole in a 1:1 ratio (13a): (80% yield); Mass spec: HRMS calc'd: $C_{56}H_{65}Cl_2N_9O_{11}S$, 1141.3898: found: 1141.3890; 1143.3860. $^1H$ and $^{13}C$ NMR are shown in FIG. 2.

Scheme 5:

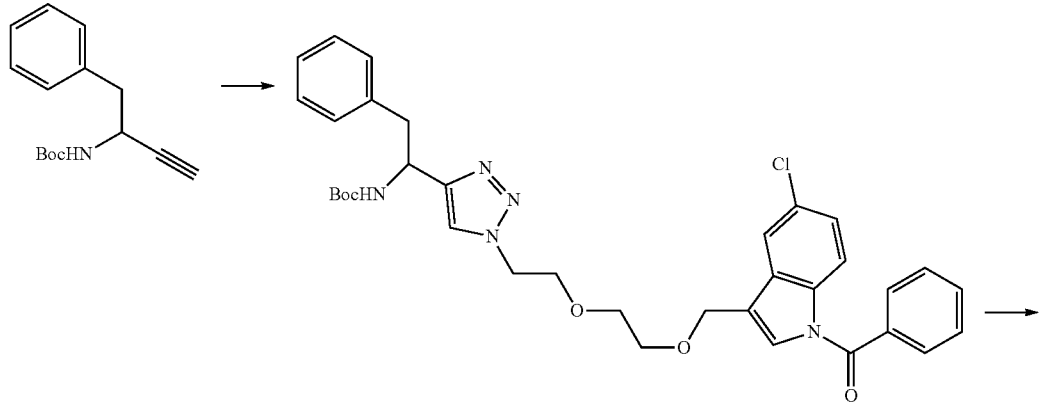

14

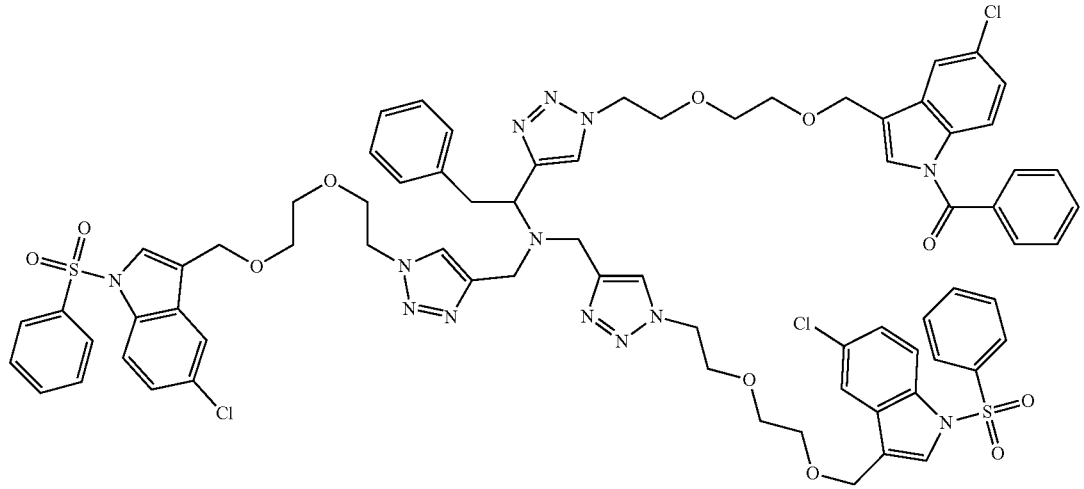

14a vii. Representative Procedure for a Huisgen [3+2] Cycloaddition Methodology Allowing Incorporation of Two Different Types of Gut-Restricted Pharmacological Agents in a 2:1 Ratio:

Synthesis of Compound (14a):

The known N-tBoc protected phenylalanyl acetylene reagent (18) was prepared according to the procedure detailed in Tetrahedron Lett., 33, 3715 (1992). It was then utilized in the [3+2] cycloaddition reaction with azide &9 under reaction conditions described here as "Method C" affording mono triazole 14 (Scheme 5): (89% mass yield); Mass spec: HRMS calc'd: $C_{35}H_{38}ClN_5O_5$, 643.2560; found: 643.2551; 644.2551.

Deprotection of t-Boc N-Phenylalanyl-2-Triazole-3-Oxa-Pentyl-5-Chloro-1-Benzyloxy Indole Intermediate 14.

An ethyl acetate (10 mL) solution of N-tert-butyl carbamate-phenylalanyl-2-substituted pentyl-triazole (0.32 mmol) pre-cooled to 0° C. was sparged with HCl gas for 1 min. The ice-bath was removed, the acidic solution allowed to warm to 23° C., and the mixture stirred for 2 h. The mixture was then concentrated to dryness to afford the de-protected intermediate 19 as its hydrochloride salt (92% mass yield), which was used without further purification.

Conversion of Intermediate 19 to 14a:

Intermediate 12 was first treated with propargyl bromide affording the corresponding propargyl amine (20), as described in EP-0 431 700 B1, and used without further purification. Intermediate 20 was then utilized in the [3+2] cycloaddition reaction with the 5-chloro-1-phenyl sulfonyl-indole pentyl azide, (9c) under reaction conditions described here as "Method C" affording the desired, single dendrimer containing two different indole-3-pegylated triazole ethers, 5-chloro-(1-(benzyloxy)-indole-3-methyleneoxa-(3-oxa-pentyl)-triazole(2-phenylalanyl)-5-chloro-(1-(phenylsulfonyl)-indole-3-methyleneoxa-(3-oxa-pentylyl)-2-amino-di-triazole in a 1:2 ratio [(14a)]: (87% yield); Mass spec: HRMS calc'd: HRMS calc'd: $C_{74}H_{72}Cl_3N_{13}O_{11}S_2$, 1487.3972; found: 1487.3946; 1489.3926. $^1H$ and $^{13}C$ NMR are shown in FIG. 3.

6. Results from the In Vivo Rodent (Rat) Distribution Experiment Designed to Monitor, and Assess, Peripheral and CNS Levels of an Orally Administered Gut-Restricted Agent, as Well as its Potential Metabolites.

Method

The standards for quantification of 11a were prepared in matching matrices, via spiking blank plasma samples or brain homogenates, with the 11a spiking solution at a ratio of 9:1. Standards were treated identically as the samples. Sprague Dawley rats were dosed [5 rats per dose] po at 50, 100 and 200 mg/kg. Plasma and brain were sampled at 30, 60 and 180 min after each dose and monitored via mass spectroscopy (CI, TS, and EI).

When exposed to a battery of cytochrome P450 enzymes in vitro, mass spectra of the resulting samples indicated the primary 11 "x" metabolites were the result of oxygen addition. Specifically, the most abundant metabolites were M1=M$^+$+16; and M2=M$^+$+32. Less abundant, although measurable, was a metabolite resulting from oxidation and "effective" loss of "2H's", which is typically observed in conversion of a methylene carbon atom into its corresponding 'oxo,' or carbonyl, oxidation state. 1-(Benzyloxy)-indole-3-methyleneoxa-(3-oxa-pentyl)-tetra-triazole-ethyl-enediamine (11a): Mass spec: HRMS calc'd: $C_{94}H_{96}N_{18}O_{12}$, 1668.7445; found: 1668.7412; 1669.7438.

TABLE 1

Quantification results for 11a and relative quantification of its two major metabolites M1 and M2 in brain and plasma samples. 30 minutes post dose.

| | Plasma Samples | | | Brain Samples | | |
|---|---|---|---|---|---|---|
| Animal ID | 11a | 11a M1 [Peak Area % to Parent] | 11a M2 [Peak Area % to Parent] | 11a | 11a M1 [Peak Area % to Parent] | 11a M2 [Peak Area % to Parent] |
| 1A v | NF | NF | NF | NF | NF | NF |
| 5A v | NF | NF | NF | NF | NF | NF |
| 9A v | NF | NF | NF | NF | NF | NF |
| 13A v | NF | NF | NF | NF | NF | NF |
| 17A v | NF | NF | NF | NF | NF | NF |
| 2B 50 | NF | NF | NF | NF | NF | NF |
| 6B 50 | NF | NF | NF | NF | NF | NF |
| 10B 50 | NF | NF | NF | NF | NF | NF |
| 14B 50 | NF | NF | NF | NF | NF | NF |
| 18B 50 | NF | NF | NF | NF | NF | NF |
| 3C 100 | NF | NF | NF | NF | NF | NF |
| 7C 100 | NF | NF | NF | NF | NF | NF |
| 11C 100 | NF | NF | NF | NF | NF | NF |
| 15C 100 | NF | NF | NF | NF | NF | NF |
| 19C 100 | NF | NF | NF | NF | NF | NF |
| 4D 100 | NF | NF | NF | NF | NF | NF |
| 8D 100 | NF | NF | NF | NF | NF | NF |
| 12D 100 | NF | NF | NF | NF | NF | NF |
| 16D 100 | NF | NF | NF | NF | NF | NF |
| 20D 100 | NF | NF | NF | NF | NF | NF |

TABLE 2

Quantification results for 11a and relative quantification of its two major metabolites M1 and M2 in brain and plasma samples. 60 minutes post dose.

| | Plasma Samples | | | Brain Samples | | |
|---|---|---|---|---|---|---|
| Animal ID | 11a | 11a M1 [Peak Area % to Parent] | 11a M2 [Peak Area % to Parent] | 11a | 11a M1 [Peak Area % to Parent] | 11a M2 [Peak Area % to Parent] |
| 1A v | NF | NF | NF | NF | NF | NF |
| 5A v | NF | NF | NF | NF | NF | NF |
| 9A v | NF | NF | NF | NF | NF | NF |
| 13A v | NF | NF | NF | NF | NF | NF |
| 17A v | NF | NF | NF | NF | NF | NF |
| 2B1 50 | NF | NF | NF | NF | NF | NF |
| 6B1 50 | NF | NF | NF | NF | NF | NF |
| 10B1 50 | NF | NF | NF | NF | NF | NF |
| 14B1 50 | NF | NF | NF | NF | NF | NF |
| 18B1 50 | NF | NF | NF | NF | NF | NF |
| 3C1 100 | NF | NF | NF | NF | NF | NF |
| 7C1 100 | NF | NF | NF | NF | NF | NF |
| 11C1 100 | NF | NF | NF | NF | NF | NF |
| 15C1 100 | NF | NF | NF | NF | NF | NF |
| 19C1 100 | NF | NF | NF | NF | NF | NF |
| 4D1 200 | NF | NF | NF | NF | NF | NF |
| 8D1 200 | NF | NF | NF | NF | NF | NF |
| 12D1 200 | NF | NF | NF | NF | NF | NF |
| 16D1 200 | NF | NF | NF | NF | NF | NF |
| 20D1 200 | NF | NF | NF | NF | NF | NF |

TABLE 3

Quantification results for 11a and relative quantification of its two major metabolites M1 and M2 in brain and plasma samples. 180 minutes post dose.

| | Plasma Samples | | | Brain Samples | | |
|---|---|---|---|---|---|---|
| Animal ID | 11a | 11a M1 [Peak Area % to Parent] | 11a M2 [Peak Area % to Parent] | 11a | 11a M1 [Peak Area % to Parent] | 11a M2 [Peak Area % to Parent] |
| 1A v | NF | NF | NF | NF | NF | NF |
| 5A v | NF | NF | NF | NF | NF | NF |
| 9A v | NF | NF | NF | NF | NF | NF |
| 13A v | NF | NF | NF | NF | NF | NF |
| 17A v | NF | NF | NF | NF | NF | NF |
| 2B2 50 | NF | NF | NF | NF | NF | NF |
| 6B2 50 | NF | NF | NF | NF | NF | NF |
| 10B2 50 | NF | NF | NF | NF | NF | NF |
| 14B2 50 | NF | NF | NF | NF | NF | NF |
| 18B2 50 | NF | NF | NF | NF | NF | NF |
| 3C2 100 | NF | NF | NF | NF | NF | NF |
| 7C2 100 | NF | NF | NF | NF | NF | NF |
| 11C2 100 | NF | NF | NF | NF | NF | NF |
| 15C2 100 | NF | NF | NF | NF | NF | NF |
| 19C2 100 | NF | NF | NF | NF | NF | NF |
| 4D2 200 | NF | NF | NF | NF | NF | NF |
| 8D2 200 | NF | NF | NF | NF | NF | NF |
| 12D2 200 | NF | NF | NF | NF | NF | NF |
| 16D2 200 | NF | NF | NF | NF | NF | NF |
| 20D2 200 | NF | NF | NF | NF | NF | NF |

Summary of Results

Neither the parent compound, nor any predicted metabolites resulting from liver-based metabolism of the parent compound, were observed at any time point of the experiment. This was found to be true for all plasma and brain samples assessed.

Exemplary Synthetic Schemes

Scheme 6

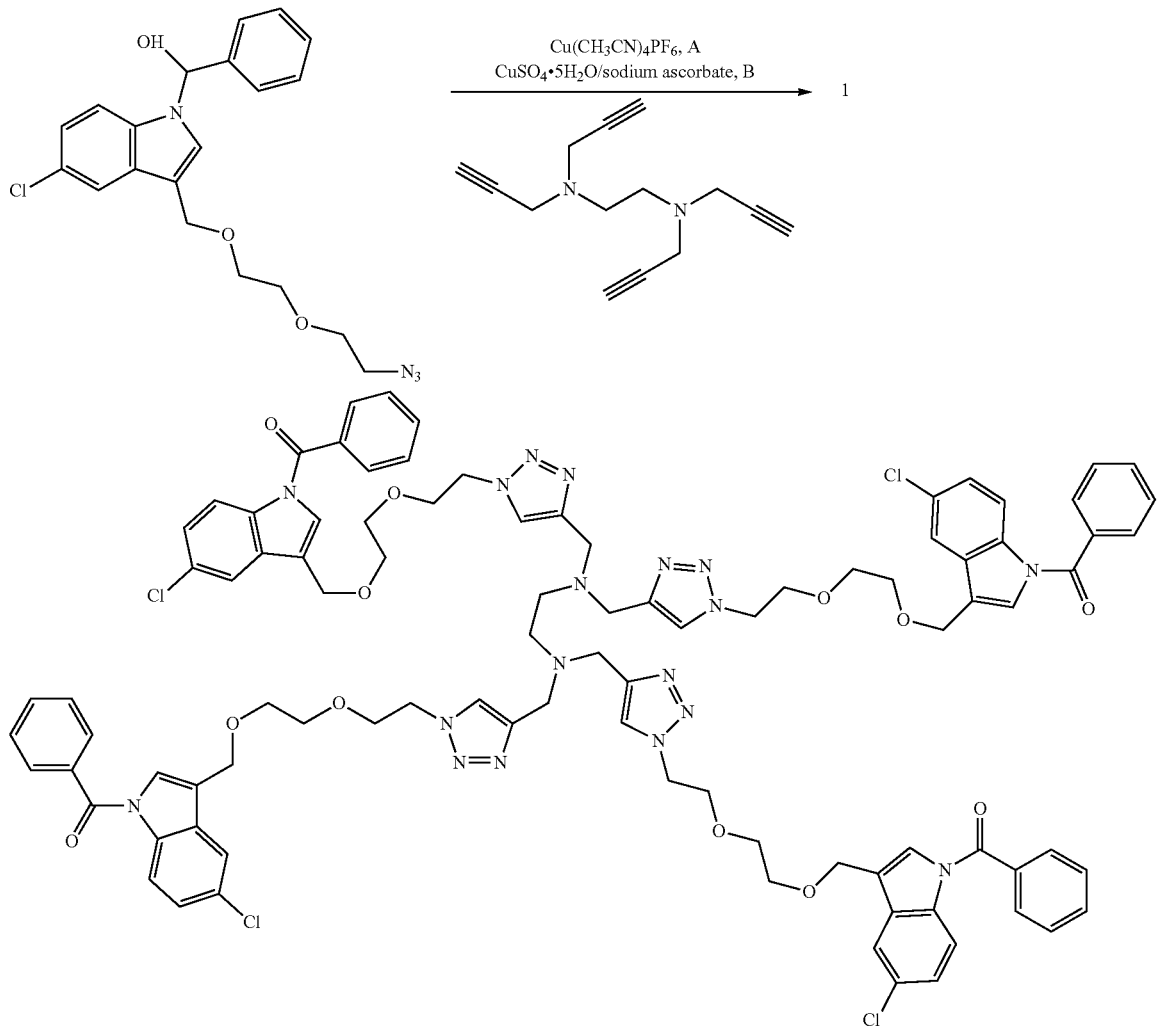

3-Methyenehydroxy indole initially was utilized to assess synthetic scheme, since it contains an N-protected ring nitrogen, a substituted 5-position and the methylenehydroxy moiety allows systematic investigation of the side-chain. For example, we were readily able to explore the tether "repeat" length and the ether linkage formation. Additionally, conversion of methylenehydroxy to nitrogen and sulfur nucleophiles enables variation of side-chain stability. Ultimately, the synthetic method described herein proceeded in high yield, with facile dendrimer formation, affording compound 1 isolated in 85% overall yield. It is noteworthy copper reagent A is preferred over B, although the overall yield using B was an acceptable [70%].

agents" necessary for detailed exploration of additivity and synergy resulting from agents recognizing different, surface-expressed molecular targets.

Dendrimer 2 also contains two different, protected indoles, which allows determination of the compatibility of various protecting group blocking/deblocking sequences, the relative ease of incorporating aza-ether tether, the overall yield for 1:1 ratio of two different agents synthesized by the variety of procedures reported herein, and the possibility of "regioisomer" preferences as a function of the specific tethers, core structures and pharmacological agent designed.

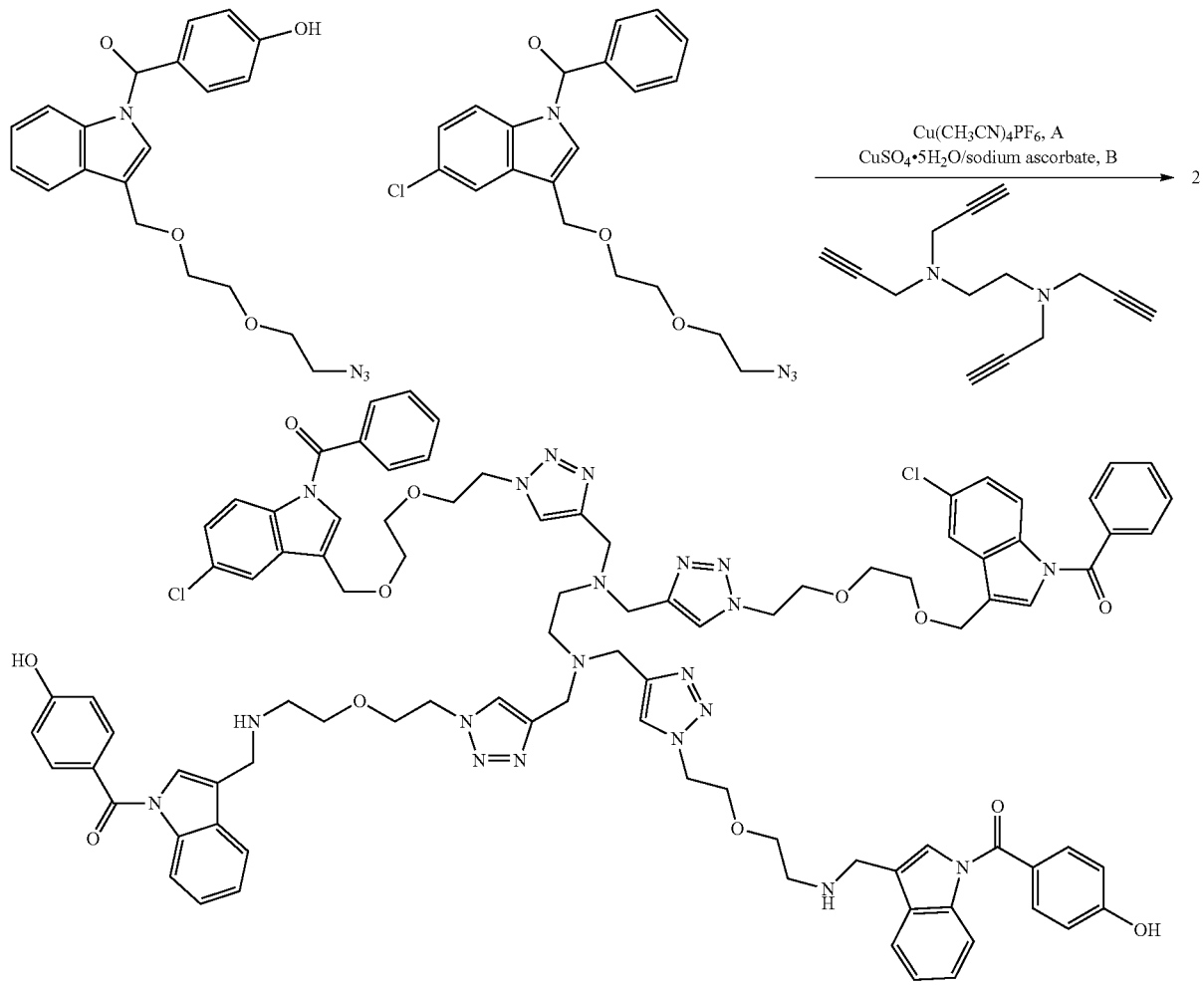

Scheme 7

Dendrimer 2 was synthesized to test the possibility of incorporating more than one pharmacological agent into one dendrimer matrix. In principle, this approach is applicable to the synthesis of dendrimers containing up to four distinct pharmacologically active components and versions containing additional multiple displays by starting from a tri- or tetra-amine starting material. This is a significant example of the uniqueness of the platform and drug discovery approach, since it exemplifies dendrimers containing multiple "active In Vivo and In Vitro Experimental Protocols and Results
In Vitro Protocols
I. In Vitro Phenotypic Screen Measuring IL-1Beta
1. Test compound and/or vehicle is pre-incubated with human peripheral blood mononuclear leukocyte (PBML, $5 \times 10^5$/ml) in AIM-V medium pH 7.4 for 2 hours. Lipopolysaccharide (LPS, 25 ng/ml) is then added to stimulate the cells overnight in 5'% $CO_2$ at 37° C.
2. Alamar Blue reagent is then added to the cells in RPMI-1640 at 37° C. for an additional 16 hour incubation period.

3. Living cells will take up Alamar Blue and emit fluorescence. Fluorescence intensity is measured using a SpectroFluor Plus plate reader with excitation at 530 nm and emission at 590 nm.
4. Decrease of 50 percent or more (50%) in fluorescence intensity relative to vehicle treated controls indicates significant cytotoxicity.
5. Compounds are screened at 10, 1, 0.1, 0.01 and 0.001 μM.
   LPS control: LPS+Veh
   Cells negative control (Veh): Veh only/No LPS
   inhibition control (DEX): Dexamethasone (100 nM, n=2)
   (Vehicle=DMSO, 0.05% v/v)
   i. At 24 hours harvest supernatants by spinning plates at 1200 rpm for 10 min, collect, and store at −80° C.
   ii. Thaw supernatants and assay for cytokine secretion with Luminex beads.
   iii. LPS-2: IL-II.
   iv. Cytokine levels are determined using a nonlinear five point parameter curve where fit=$(A+((B-A)/(1+(((B-E)/(E-A))*((x/C)^D)))))$ for interpolation of data. EC50 values are then calculated off of interpolated data using nonlinear regression to fit data to the Dose-Response, One-Site Model where: $y=A+[(B-A)/1+((C/x)^D))]$.

II. TLR4 In Vitro Functional Screen Inhibition and/or Antagonism

TLR4 Reporter Assay Protocol
1. To specifically evaluate the inhibitory activity of the selected compounds towards TLR4 signaling a HEK-Blue™-hTLR4 reporter cell line (InvivoGen) is used, which selectively expresses the TLR4 receptor and activates secreted embryonic alkaline phosphatase (SEAP) as a reporter gene via TLR4 agonists.
2. The antagonism of these compounds is assessed as indicated by the manufacturer. The negative control comprised only the TLR4 agonist lipopolysaccharide (LPS) (Sigma Aldrich, St Louis, Mo., USA). For the positive control, the commercially available TLR4 inhibitor TAK-242 is selected and used according to the manufacturer (InvivoGen) instructions.
3. To evaluate the antagonistic effects of compounds, the cells are cultured as specified by the provider (InvivoGen). The cells are then pre-incubated with these compounds for 2 h at 37° C. at various concentrations. Afterward, the cells are challenged with LPS for 20 h.

III. TGR5 In Vitro Assay Protocol
1. hTGR5/CRE/HEK293 or mTGR5/CRE/HEK293 stable cell line is obtained by transfection of HEK293 cells with human or mouse TGR5 expression plasmid (hTGR5-pcDNA 3.1 or mTGR5-pcDNA 3.1) and CRE-driven luciferase reporter plasmid (pGL 4.29, Promega, Madison, Wis.), and employed to assess the activity of test compounds by reporter gene assay.
2. Cells are seeded into 96-well plates and incubated overnight in DMEM supplemented with 10% FBS in 5% $CO_2$ at 37° C. Then, cells are incubated with fresh medium containing different concentrations of test compounds (20 mM oleanolic acid as positive control) for 5.5 h. Luciferase activity in cell lysate is determined using the Steady-Glo Luciferase Assay System (Promega, Madison, Wis.) according to the manufacturer's instructions.

In Vivo Protocols

IV. TNBS/DSS Protocol Utilizing Anti-Inflammatory Bosentan as Positive Control
1. At 24 and 2 h prior to induction of colitis, rats are treated with the oral preparation of bosentan (10, 30 or 60 mg/kg p.o.) suspended in 5% gum arabic (vehicle). Bosentan is administered twice prior to induction of colitis to ensure that adequate plasma levels of bosentan are present (Clozel et al., 1994). All rats are treated once daily thereafter for 5 days. To determine the efficacy of the compound after the initiation of inflammation, bosentan (10, 30 or 60 mg/kg p.o.) is administered 1 h after the induction of colitis and once daily for 5 days. In both treatment regimens, appropriate vehicle controls are administered in the same manner.
2. Uninflamed rats are also treated with bosentan (60 mg/kg p.o.) in a manner similar to that employed in the pre-dose groups receiving trinitrobenzene sulphonic acid in ethanol. These rats are monitored over the dosing period for any changes in fecal consistency.

V. Induction and Macroscopic Evaluation of Inflammation
1. Male Sprague-Dawley rats (250-260 g) are lightly anesthetized with ether. A rubber catheter (OD, 2 mm) is inserted rectally into the colon such that the tip is 8 cm proximal to the anus, approximately at the splenic flexture. TNBS dissolved in 50% (v/v) aqueous ethanol is instilled into the colon via the rubber cannula (20 mg/0.35 mL/rat). For macroscopic evaluation of inflammation, colonic damage score (CDS) and myeloperoxidase (MPO) activity are measured as described previously (Honget al., 2012).
2. The modified scoring system for CDS is as follows:
   i. Normal appearance, 0;
   ii. Localized hyperemia but no ulcer, 1;
   iii. Linear ulcers without significant inflammation, 2;
   iv. 2-4 cm site of inflammation and ulceration with scab, 3;
   v. Serosal adhesion to other organs, 2-4 cm site of inflammation and ulceration with scab, 4:
   vi. Stricture, serosal adhesion involving several bowel loops, <4 cm site of inflammation and ulceration with scab, 5.

VI. DIO Rodent Model Protocol
1. Sixty-five CS7BL/6J mice (4-6 weeks of age) will be ordered from Charles River UK Limited, Margate. Kent, UK. Mice will be group housed at Charles River UK Limited with free access to a high fat diet (D12451 45% of Kcal derived from fat; Research Diets, New Jersey, USA) and tap water at all times. Animals will be maintained on a normal phase 12 h light-dark cycle (lights on 07:00). During this time body weight will be recorded weekly.
2. Animals are exposed to the high fat diet for 14 weeks. They are transferred to facilities where they will be singly housed in polypropylene cages for a further three week period and placed on reverse phase lighting (lights off for 8 h from 09:30-17:30 h) during which time the room will be illuminated by red light. During the third week, animals undergo daily handling (animals are handled as if to be dosed but are actually not weighed or dosed). This improves the stability of the body weight response during the baseline phase. Animals are dosed with vehicle orally once daily for a 7 day baseline period. Body weight and food and water intake are recorded daily. On Day −3 during this baseline period (after the completion of dosing on that day), a blood sample (approx. 40 uL) is taken from the lateral tail vein using lithium heparin coated collection tubes (Sarstedt CB300LH). The sample is spun in a cooled centrifuge (4° C.) and the plasma fraction collected and frozen. The sample is assayed for glucose and insulin content. Towards the end of the baseline treatment, animals are weighed and allocated into 5 treatment groups matched, as closely as possible, for body weight and baseline glucose and insulin. At this stage fifteen animals are set aside as spares and will not progress to the dosing phase of this particular study. The criteria for withdrawing the animals include general condition, the body weight response to baseline dosing (e.g. poor condition, excessive weight loss), and outlying plasma insulin and glucose values. Subsequently, mice are dosed once daily for 6 days with vehicle or test drug.

3. All treatments are dosed orally by gavage. During the baseline and treatment period food intake, water intake and body weight are recorded daily. At the completion of dosing animals are examined and any overt behavior is recorded. Dosing begins at approximately 08:45 each day.

4. On day 6, all the mice are fasted at 16:00. On Day 7 the mice undergo an OGTT. Each animal is dosed with vehicle or test compound and 60 minutes later is dosed with D-glucose (2 g/kg po). A baseline blood sample is taken immediately before the glucose load and further blood samples are taken 15, 30 and 60 minutes post glucose administration. All blood samples (approximately 30 mL, with the exception of the baseline samples which are slightly larger) are taken from the tail vein. Blood samples are taken into lithium heparinised tubes (Sarstedt Microvette CB300) and plasma separated by centrifugation. Plasma samples are frozen at −80° C. and subsequently they are assayed for glucose and insulin using commercially available kits and reagents. Food is re-presented subsequent to the OGTT and final readings are taken on the morning of Day 8. If necessary, animals are re-used after a suitable interval (a minimum of 1 week).

5. Results: body weights, food intake and water intake are expressed as mean values±SEM. Body weight and food and water intake data are analysed by ANCOVA followed by appropriate comparisons (two-tailed) to determine significant differences from the control group. $P<0.05$ is considered to be statistically significant. The exact statistical tests depend upon the data; however, the effects of drugs on plasma levels of insulin and glucose in OGTT are normally determined by robust regression.

VII. Gut-Restriction Platform Applicability to the Treatment of CRC

DSS Rodent Utility as a CRC Disease Model

There is now a great deal of data supporting the notion intestinal tumors likely originate from normal ISC's [Intestinal Stem Cells] and chronic inflammation is a predisposing factor to CRC. For example, TLR-deficient mice have been shown to exhibit a reduced rate of tumorigenesis in mouse models of colitis-associated cancer and CRC. Furthermore, intestinal epithelial cell-specific constitutive activation of NF-κB significantly accelerates APC-driven tumor formation. Since NF-κB is a major pathway downstream of the cell surface-expressed TLRs, it is reasonable to propose antagonists versus several of the TLR's, and particularly TLR-4, as potential CRC treatments. Inflammation is an underlying causation of disease or at the very least the primary driver for predisposition to disease. Since a range of gut-expressed molecular targets, many of which are nutrient sensing, clearly effect the overall concentration of pro-inflammatory cytokines not only locally in the intestine and in the intestinal microbiota, but also systemically, it is very reasonable to hypothesize anticipated disease modifying effects resulting from treating patients with agonists, or antagonists, of several gut-expressed GPCR's. Finally, the potential disease-relevant effects, which are attributable to dysregulation of a number of pro-inflammatory cytokines ultimately controlled by the gut-expressed nutrient sensing GPCR molecular targets, may optimally observed for combinations of agents and not a single agent. Thus, ISC transplantation, antagonism of several Pattern Recognition Receptors, an example of the PRR's is TLR-4, agonism of specific nutrient sensing GRCR's, one example is the nicotinic acid receptor GPR109a, antagonism of the GPCR H4 receptor, and microbiota engineering are all potential clinical approaches to the treatment of CRC.

VIII. GPR109a Agonist In Vivo Experiment

Agonists of the surface-expressed molecular target GPR109a protect against weight loss and diarrhea caused by DSS treatment of mice previously exposed to antibiotics. The mouse in vivo experiment determines the efficacy of gut restricted GPR109a agonists in protecting against DSS colitis in the absence of endogenous ligand.

Protocol

1. GROUP 1 (8 mice): No antibiotic treatment+Drug (200 mg/kg)

GROUP 2 (8 mice): Antibiotic treatment+Vehicle

GROUP 3 (8 mice): Antibiotic treatment+Drug (200 mg/kg)

All mice are exposed to DSS.

2. Antibiotic treatment is as follows: Ampicillin, Metronidazole, Neomycin. Gentamicin (all doses 1 g/L), and Vancomycin (dose 0.5 g/L) are administered once daily by oral gavage.

3. A preliminary experiment determines precise kinetics of antibiotic DSS colitis model prior to drug study initiation.

4. Data in the GPR109−/− mouse suggests a mechanism involving both hematopoietic cells (Tregs, IL-10, DCs) and epithelial cells (IL-18).

5. In the DSS injury model the known GPR109 agonist, niacin, had a dramatic effect when mice were pretreated with antibiotics.

6. To observe a full effect in the DSS model (including recovery phase) it is necessary to treat for 3-4 weeks total.

REFERENCES

Kolb et al (2001) Angew. Chem. Int. Ed. 40:2004-2021;
Kolb et al (2003) Drug Discovery Today 8:1128-1137;
Rostovtsev et al (2002) Angew. Chem. Int. Ed. 41:2596-2599;
Tornoe et al (2002) Jour. of Org. Chem. 67:3057-3064;
Wang et al (2003) Jour. of the Am. Chem. Soc. 125:3192-3193:
Lee et al (2003) Jour. of the Am. Chem. Soc. 125:9588-9589;
Lewis et al (2002) Angew. Chem., Int. Ed. 41:1053-1057;
Manetsch et al (2004) Jour. of the Am. Chem. Soc. 126:12809-12818;
Mocharla et al (2005) Angew. Chem. Int. Ed. 44:116-120;
Whiting et al (2006) Angew. Chem. 118:1463-1467;
Whiting et al (2006) Angew. Chem. Int. Ed. Engl. 45:1435-1439:
McDonaugh and Murphy (2013) Tetrahedron, web edition;
Henning and Witman (2007) Organic Letters 9:1;
Peetz, et al (2008) Tetrahedron Letters 49:6386-6389.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control. The compounds, synthetic methods, and experimental protocols and results of U.S. application Ser. No. 13/680,582, filed Nov. 19, 2012, are hereby incorporated by reference.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound, comprising:
a scaffold having a structure of the formula:

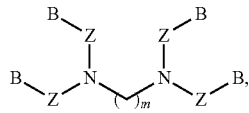

wherein:
Z represents, independently for each occurrence, a bond, $(C_{1-10})$alkyl, $(C_{6-14})$aryl, $(C_{6-14})$aryl$(C_{1-10})$alkyl, $(C_{2-10})$alkenyl, $(C_{2-10})$alkynyl;
m is an integer from 0 to 10; and
B represents a branch terminating in a pharmacophore having an affinity for a receptor expressed in a gastrointestinal tract, or a pharmaceutically acceptable salt thereof;
wherein each branch
independently comprises —Y—$(C_{1-20})$alkyl- or —Y—$(CH_2CH_2X)_n$—, wherein:
X, independently for each occurrence, represents O, S, SO, $SO_2$, NH, N($C_{6-14}$ aryl), N($C_{1-20}$ alkyl), or N(($C_{1-20}$)alkyl($C_{6-14}$ aryl));
Y is, independently for each occurrence, an optionally substituted triazole; and
n is an integer from 1 to 20;
wherein bonds linking the pharmacophores to the scaffold are not hydrolyzed under physiologic conditions;
wherein the receptor is a PRR-type receptor, a bile acid receptor, a taste receptor, an olfactory receptor, a TGR-type receptor, or a GPR-type receptor; and
wherein the compound weighs less than about 10,000 Daltons.

2. The compound of claim 1, wherein the scaffold is hydrophilic.

3. The compound of claim 1, wherein the plurality of pharmacophores are hydrophobic.

4. The compound of claim 1, wherein each branch terminates in a pharmacophore.

5. The compound of claim 1, wherein every pharmacophore is identical.

6. The compound of claim 1, wherein the bonds linking the pharmacophores to the scaffold are not hydrolyzed under the conditions of the gastrointestinal tract.

7. The compound of claim 1, wherein each branch is hydrophilic.

8. The compound of claim 1, wherein the scaffold is a dendrimer.

9. A pharmaceutical composition, comprising a compound of claim 1 and one or more pharmaceutically acceptable excipients.

* * * * *